(12) United States Patent
Li et al.

(10) Patent No.: US 9,650,390 B2
(45) Date of Patent: May 16, 2017

(54) WATER-SOLUBLE TAXANE DERIVATIVES AND USES THEREOF

(71) Applicant: JIANGSU NHWALUOKANG PHARMCEUTICAL RESEARCH AND DEVELOPMENT CO., LTD, Xuzhou, Jiangsu (CN)

(72) Inventors: Qingeng Li, Chongqing (CN); Tao Wang, Chongqing (CN); Gang Chen, Chongqing (CN); Yuanzhong Wang, Chongqing (CN); Wei Mao, Chongqing (CN); Lingguo Zeng, Chongqing (CN); Tong Wu, Chongqing (CN); Dahai Chen, Chongqing (CN)

(73) Assignee: JIANGSU NHWALUOKANG PHARMCEUTICAL RESEARCH AND DEVELOPMENT CO., LTD, Xuzhou (CN)

( * ) Notice: Subject to any disclaimer, the term of this patent is extended or adjusted under 35 U.S.C. 154(b) by 0 days.

(21) Appl. No.: 15/119,603

(22) PCT Filed: Feb. 16, 2015

(86) PCT No.: PCT/CN2015/073178
§ 371 (c)(1),
(2) Date: Aug. 17, 2016

(87) PCT Pub. No.: WO2015/120822
PCT Pub. Date: Aug. 20, 2015

(65) Prior Publication Data
US 2017/0057973 A1    Mar. 2, 2017

(30) Foreign Application Priority Data

Feb. 17, 2014  (CN) .......................... 2014 1 0053129
Mar. 19, 2014  (CN) .......................... 2014 1 0102551
(Continued)

(51) Int. Cl.
*C07D 493/04* (2006.01)
*C07D 305/14* (2006.01)
(Continued)

(52) U.S. Cl.
CPC ......... *C07D 493/04* (2013.01); *C07D 305/14* (2013.01)

(58) Field of Classification Search
CPC combination set(s) only.
See application file for complete search history.

(56) References Cited

FOREIGN PATENT DOCUMENTS

CN    1709516 A        12/2005
CN    1895676 A    *   1/2007
CN    1895676 A        1/2007

OTHER PUBLICATIONS

Xie et al. "Mitochondrial-targeted prodrug cancer therapy using a rhodamine B labeled fluorinated docetaxel" Eur. J. Pharm. Biopharm. 2013, 85, 541-549.*
(Continued)

*Primary Examiner* — Michael Barker
*Assistant Examiner* — Amanda L Aguirre
(74) *Attorney, Agent, or Firm* — Schwegman Lundberg & Woessner, P.A.

(57) ABSTRACT

The present invention discloses a class of water soluble taxane derivatives, a method for treating tumor using the same, use thereof as anti-tumor drugs and use thereof in the preparation of anti-tumor drugs. The water soluble taxane derivatives have the general formula (I-1), (I-2) or (I-3): wherein, $R^1$ is H or methyl; $R^2$ is H, methyl or acetyl; $R^3$ is phenyl or $OC(CH_3)_3$; X is H, $C_{1-6}$ alkyl or F; Y is F or $C_{1-6}$ alkyl substituted with one or more F; n is 1, 2, 3, 4, 5 or 6; W is $NR^4R^5$.A or

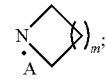

$R^4$ and $R^5$ are each independently H, $C_{1-6}$ alkyl optionally substituted with phenyl, or $C_{3-6}$ cycloalkyl; m is 0, 1, 2 or 3; and A is a pharmaceutically acceptable acid.

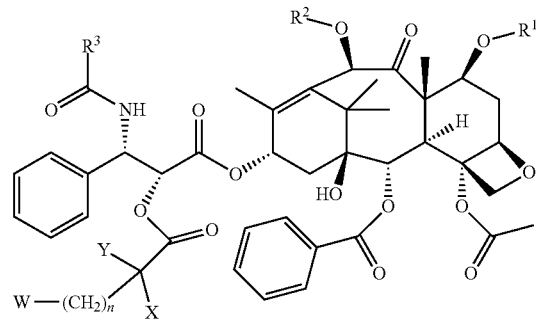

(I-1)

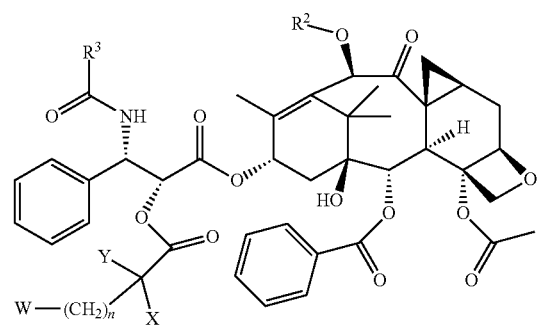

(I-2)

(Continued)

-continued (I-3)

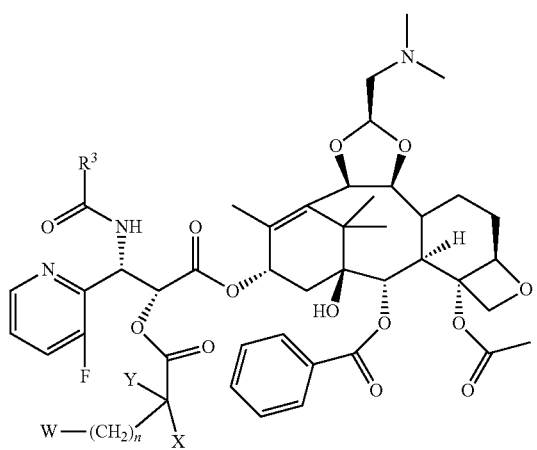

14 Claims, No Drawings

(30) Foreign Application Priority Data

Apr. 17, 2014 (CN) .......................... 2014 1 0154956
Apr. 17, 2014 (CN) .......................... 2014 1 0155204

(51) Int. Cl.
*A61K 31/337* (2006.01)
*A61K 31/443* (2006.01)

(56) References Cited

OTHER PUBLICATIONS

"International Application No. PCT/CN2015/073178, International Search Report mailed May 21, 2015", w/ English Translation, (May 21, 2015), 7 pgs.
"International Application No. PCT/CN2015/073178, Written Opinion mailed May 21, 2015", (May 21, 2015), 4 pgs.

* cited by examiner

WATER-SOLUBLE TAXANE DERIVATIVES AND USES THEREOF

CROSS-REFERENCE TO RELATED APPLICATIONS

The present application is a U.S. National Stage Filing under 35 U.S.C. 371 from International Application No. PCT/CN2015/073178, filed on Feb. 16, 2015, and published as WO 2015/120822 on Aug. 20, 2015, which claims the benefit of priority from Chinese patent application No. 201410053129.9 filed on Feb. 17, 2014, Chinese patent application No. 201410102551.9 filed on Mar. 19, 2014, and Chinese patent application Nos. 201410154956.7 and 201410155204.2 filed on Apr. 17, 2014, the contents of which are incorporated herein by reference.

TECHNICAL FIELD

The present invention relates to the field of pharmacy, specifically to water soluble taxane derivatives, a method for treating tumor using the same, use thereof as antitumor drugs, and use thereof in the preparation of antitumor drugs.

BACKGROUND ART

A prodrug, also referred to as a precursor of a drug, refers to a compound which achieves pharmacological action after the conversion in an organism. A prodrug per se has no or little bioactivity, and releases an active agent after metabolism in vivo. The purpose of investigating and preparing a prodrug is to increase the bioavailability, modify the solubility, enhance the targeting properties, or reduce the toxicity or side effects of the parent drug. It is advantageous for many drugs, especially those having low bioavailability, poor water solubility or high toxic side effects, to be prepared into prodrugs. In general, it is required in clinic that a prodrug can be quickly dissociated into a ligand and a parent drug after entering the body, and the ligand is non-toxic. The parent drug thus released can exert pharmaceutical effects, and the non-toxic ligand is of no harm to the body.

Taxane drugs (including those in clinical stage) with antitumor activity have the following parent structures:

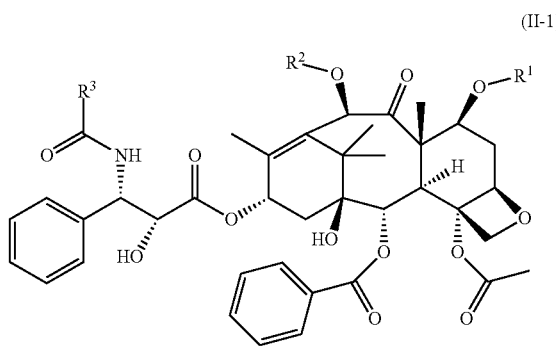

(II-1)

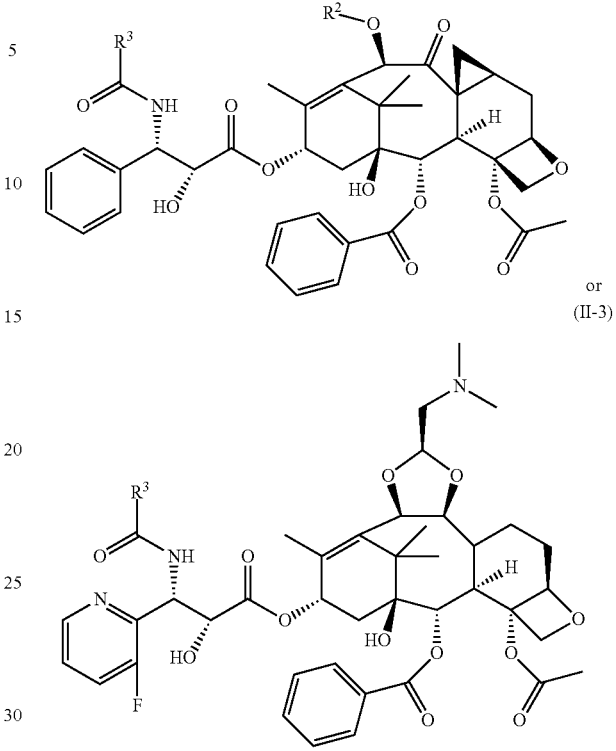

(II-2)

or (II-3)

wherein $R^1$ is H or methyl; $R^2$ is H, methyl or acetyl; $R^3$ is phenyl or $OC(CH_3)_3$.

Among these drugs, paclitaxel, docetaxel and cabazitaxel are most widely used in clinic.

| Name | Parent Structure | $R^1$ | $R^2$ | $R^3$ |
|---|---|---|---|---|
| paclitaxel | (II-1) | H | Ac | Ph |
| docetaxel | (II-1) | H | H | $OC(CH_3)_3$ |
| cabazitaxel | (II-1) | Me | Me | $OC(CH_3)_3$ |
| larotaxel | (II-2) | | Ac | $OC(CH_3)_3$ |
| tesetaxel | (II-3) | | | $OC(CH_3)_3$ |

Taxane drugs have good antitumor activity. However, they have poor water solubility and low oral bioavailability, and thus can only be administered via intravenous injection in clinic. In clinic, nonionic surfactants, such as polyethoxylated castor oil or Tween-80, are often added to this class of compounds as co-solvents to prepare an injection. Unfortunately, such surfactants usually cause side effects, such as vasodilatation, reduced blood pressure, liver toxicity, severe allergic reactions and the like, which highly limit the clinical application of taxane drugs. As such, many pharmacists worldwide have tried to solve this problem by formulation improvement and structural modification.

With respect to the preparations of paclitaxel, references can be referred to the following: in 1995, Robert et al. described "Stable oil-in-water emulsions incorporating a taxane (taxol) and method of making same" (CN 1153474); in 1996, Hairu Zhang et al. described "Water soluble powder for injection of paclitaxel and preparation method thereof" (CN 96112502); in 1998, J. M. Géczy described "Pharmaceutical compositions containing cyclodextrins and taxoids" (Application No./Patent No. 98811010); in 1999, Rubinfeld, Joseph et al. described "Water-miscible pharmaceutical compositions of paclitaxel" (CN99812662), Guoying Weng et al. described "Lipid compositions of paclitaxel and preparation method thereof" (CN0019039), Yingjin Yuan et al. described "Prodrugs of paclitaxel or docetaxel supported by polyethylene glycol" (CN00109748), in 2001, Junqi Pan et al. described "A nanosized magnetic targeting preparation of paclitaxel and preparation method thereof" (CN01128733); in 2002, Bin Zhu et al. described "A preparation method of a nanoparticle of paclitaxel" (CN02133333), Jialin Yan et al. described "A novel preparation of an antitumor drug—a microemulsion of paclitaxel" (CN02153674); in 2003, Yu Liu et al. described "A water soluble complex of an antitumor drug, paclitaxel, and preparation method thereof" (CN03119497); in 2006, Xianghua Liu et al. described "A composition of paclitaxel/docetaxel liposomes and preparation method thereof" (CN200610137900), Shihai Li et al. described "A lipid microsphere injection of paclitaxel and preparation method thereof" (CN200610165800), Xiuguo Zhang et al. described "An intravenous injection solution of paclitaxel and application thereof" (CN200610165508); in 2007, Yunqing Kang et al. described "A paclitaxel loaded sustained release microsphere prepared by supercritical fluids technology" (CN200710049845), Fang Li et al. described "A nanoparticle of paclitaxel and preparation and application thereof" (CN200710047767); and in 2008, Dingquan Yao et al. described "A water soluble injection composition of paclitaxel, preparation and application thereof" (CN200810232882), Yuling Liu et al. described "A lipid composition of paclitaxel" (CN200810168213). However, all the above preparations have several disadvantages, and the clinical application thereof is limited.

With respect to the preparations of docetaxel, references can be referred to the following: Immordino et al. prepared liposomes containing docetaxel through a film dispersion method (Immordino M L, Brusa P, Arpicco S. et al., Preparation, characterization, cytotoxicity and pharmacokinetics of liposomes containing docetaxel, J. Controlled Release, 2003, 91 (4):417-429); LIVERSIDGE, Gary et al. prepared nanoparticulate preparations of docetaxel or analogue thereof (CN200680012670.9); Shaohui Zheng et al. investigated sub-microemulsion for intravenous injection of docetaxel and preparation method thereof (CN200610012102); Yuqing Xu et al. prepared a magnetic microsphere of docetaxel by a heat-curing method (Yuqing Xu, Xuemei Wen, A preparation method of a magnetic microsphere of docetaxel, Journal of Harbin Medical University, 2005, 39(6):537-539; Yuqing Xu, Xuemei Wen, a magnetic microsphere of docetaxel and preparation method thereof, CN200410044113); Zhenxin Du et al. prepared a lipid emulsion of docetaxel (Zhenxin Du, Xiulian Lu, Datao Li et al., A lipid emulsion containing docetaxel and preparation method thereof, CN 200510084055); Jakateet al. prepared fibrlnogen-coated olive oil droplets with a drug loading of 1.0 g/l (Jakate A S, Einhaus C M, DeAnglis A P. et al., preparation, characterization, and preliminary application of fibrinogen-coated olive oil droplets for the targeted delivery of docetaxel to solid malignancies, Cancer Res, 2003, 63(21):7314-7320); and Le Garreeet al. prepared a PVP-b-PDLLA polymeric micelle of docetaxel (Le Garree D, Gori S, Luo L. et al., Poly(N-vinylpyrrolidone)-block-poly(d,l-lactide) as new polymeric solubilizer for hydrophobic anticancer drugs: in vitro and in vivo evaluation, J Controlled Release, 2004, 99(1):83-101). All the above technologies are attempts for solving problems of taxane drugs currently used in clinic by formulation means, but with limited success.

The only successful water soluble preparation of taxane drugs is Albumin-bound paclitaxel marketed in 2005. Although this preparation does not contain a high molecular solvent, bubbles can be easily produced during formulating before injection due to the surfactant properties of albumin, and thus its application is not convenient.

Meanwhile, pharmaceutical chemists have focused on structural modification of taxane drugs. The main strategy for preparing water soluble derivatives of taxane drugs is to introduce hydrophilic groups to the 2'-OH or 7-OH in paclitaxel. Due to the high steric hindrance of 7-OH in paclitaxel, dissociation is difficult to occur after introduction of the groups at this position, and thus the compound obtained is unlikely to be used as a prodrug. The 2'-OH in taxane drugs is considered as an essential pharmacological group, and introduction of the groups to this position would result in decrease of efficacy. But the steric hindrance at this position is low, which would facilitate the dissociation. Pharmaceutical chemists have prepared many derivatives of paclitaxel and docetaxel (see e.g., Margri N F, Kingston D G I. J Nat Prod, 1988, 51:298; Journal of Medicinal Chemistry (1989), 32(4), 788-92; U.S. Pat. No. 4,960,790; Zhao Z. Kingston D G I. J Nat Prod, 1991, 54:1607; Mathew A, Mejillano M R, et al., J Med Chem, 1992, 35:4230; Nicolaon K C, Riemer C, Kerr M A, et al., Nature, 1993, 364:464; Nicolaon K C, Guy R K, Pitsinos E N, et al., Angew Chem Int Ed Engl, 1994, 33:1583; Chemistry & Biology 1995, 2 (4):223-227; JP09110865; J. Med Chem. 2000, 43, 3093-3102; Mendleev. Commun., 2001, 11(6):276-217; Biological & Pharmaceutical Bulletin (2002), 25(5), 632-641; J. Org. Chem., 2003, 68, 4894-4896; U.S. Pat. No. 6,649,778; CN200410002722; JP2006193627; Alaoui A. E., Saha N., Schmidt F., Monneret C. New Taxol (paclitaxel) prodrugs designed for ADEPT and PMT strategies in cancer chemotherapy, Bioog Med. Chem., 2006, 14:5012-5019; Bioorg. Med. Chem. Lett. 17 (2007) 2894-2898; Pharmaceutical Research, 26(4):785-793, 2009; Bioconjugate Chem. 2009, 20, 2214-2221; Pharmaceutical Research, 2010, 27(2):380-389; J. Med. Chem., 1997, 40(26):4319-28; J. Med Chem., 1996, 39(7):1555-9; Journal of Tianjin University, 2000, 33(1):51-5; Chemical Journal of Chinese Universities, 2000, 21(3): 401-6; EP524093, 1993; WO9623779; WO9802426; U.S. Pat. No. 6,025,385; WO9914209; U.S. Pat. No. 6,136, 808; US20020052403; CN200610171580; Wenting Du, Lan Hong, Tongwei Yao, et al, Synthesis and evaluation of water-soluble docetaxelprodrugs-docetaxel esters of malic acid, Bioorganic & Medicinal Chemistry, 2007, 15(18), 6323-6330; CN200510027736.9; CN200510040320; WO2009141738; Chemistry & Biology 1995, 2 (4):223-227). However, no further reports regarding the derivatives have been found.

Since no substantial progress has been achieved in the investigations of water soluble derivatives of paclitaxel and docetaxel, no reports on the water soluble derivatives of subsequent taxane drugs, i.e., cabazitaxel, larotaxel and tesetaxel, have been found.

Although much effort has been made to the structural modification of taxane drugs by pharmaceutical chemists, no taxane derivative having good water solubility and easy dissociation in vivo has been found.

SUMMARY OF THE INVENTION

In a first aspect, the present invention provides a carboxylic acid derivative or a salt thereof useful as a ligand for the preparation of a water soluble paclitaxel prodrug which has good water solubility and can be quickly dissociated in vivo and release the parent drug, so as to exert effects.

The carboxylic acid derivative of the present invention has following general formula (III):

(III)

wherein,

X is H, $C_{1-6}$ alkyl or F;

Y is F or $C_{1-6}$ alkyl substituted with one or more F;

n is 1, 2, 3, 4, 5 or 6;

$W^1$ is $NR^4R^4$, $NR^4R^5 \cdot B$,

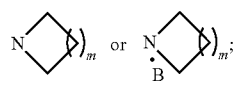

$R^4$ and $R^5$ are each independently H, $C_{1-6}$ alkyl optionally substituted with phenyl, or $C_{3-6}$ cycloalkyl;

m is 0, 1, 2 or 3;

B is an acid; and

D is hydroxyl, Cl or Br.

According to an embodiment of the present invention, X is H, methyl or F.

According to an embodiment of the present invention, Y is F, $CF_3$ or $CHF_2$.

According to an embodiment of the present invention, $R^4$, $R^5$ are each independently H, methyl, ethyl, propyl, isopropyl, butyl, isobutyl, benzyl, cyclopropyl, cyclobutyl, cyclopentyl or cyclohexyl.

According to an embodiment of the present invention, the acid B is an acid which can form a salt with amine, such as hydrochloric acid, hydrobromic acid, sulfuric acid, phosphoric acid, trifluoroacetic acid, difluoroacetic acid, fluoroacetic acid, acetic acid, benzensulfonic acid or p-toluene sulfonic acid.

According to an embodiment of the present invention, when X and Y are different (i.e., the α-C of the carboxyl in the carboxylic acid derivative is a chiral atom), the carbon atom to which both X and Y are attached is in a single R configuration, in a single S configuration, or in both R and S configurations.

According to an embodiment of the present invention, the carboxylic acid derivative of the present invention is selected from the group consisting of:

4-N,N-dimethylamino-2(R)-fluorobutyric acid hydrochloride;

4-N-isopropylamino-2(R,S)-fluorobutyric acid hydrochloride;

4-N,N-diethylamino-2(R,S)-trifluoromethylbutyric acid hydrochloride;

4-N-benzylamino-2,2-difluorobutyric acid hydrochloride;

4-N-isobutylamino-2(R,S)-difluoromethylbutyric acid hydrochloride;

4-N-(aziridin-1-yl)-2(R,S)-difluoromethylbutyric acid hydrochloride;

4-N-(pyrrolidin-1-yl)-2(R,S)-fluorobutyric acid hydrochloride;

3-N-benzylamino-2(R,S)-(1,1-difluoromethyl)propionic acid hydrochloride;

6-N-cyclohexylamino-2(R,S)-trifluoromethylhexanoic acid hydrochloride;

sodium 4-N,N-dimethylamino-2(R,S)-fluorobutyrate;

calcium 4-N, N-diethylamino-2(R,S)-fluorobutyrate;

aluminum 3-N-benzylamnino-2(R,S)-benzyloxypropionate;

4-N,N-dimethylamino-2(R,S)-fluorobutyryl chloride hydrochloride;

4-N-benzylamino-2,2-difluorobutyryl chloride hydrochloride;

4-N,N-dimethylamino-2(R,S)-fluorobutyric acid; and

4-N,N-dimethylamino-2(S)-fluorobutyric acid hydrochloride.

In a second aspect, the present invention provides water soluble taxane derivatives. The water soluble taxane derivatives have stable chemical properties and good water solubility. These water soluble taxane derivatives are a series of amine-containing salt compounds prepared by a reaction between the hydroxyl group at position 2' in taxane compounds and amino acids.

The water soluble taxane derivative of the present invention has following general formula (I-1), (I-2) or (I-3):

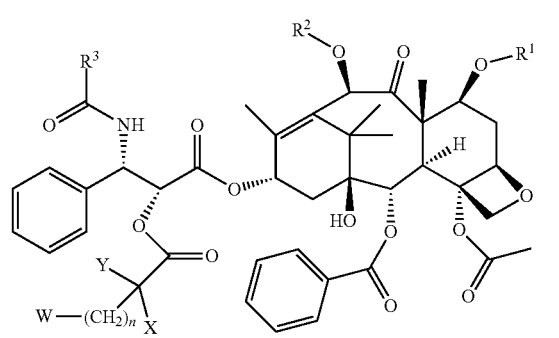

(I-1)

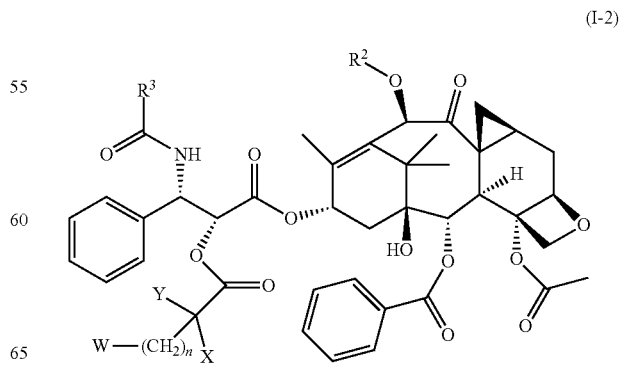

(I-2)

-continued (I-3)

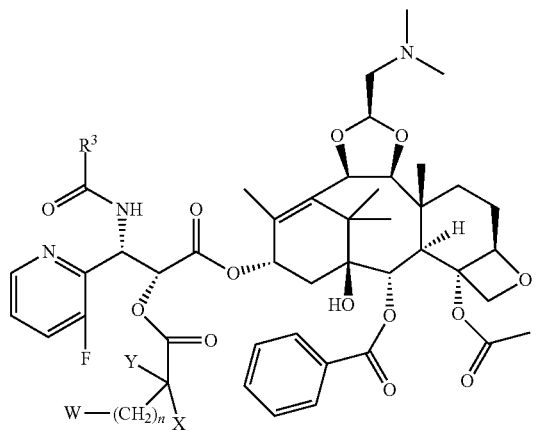

wherein,
R[1] is H or methyl;
R[2] is H, methyl or acetyl;
R[3] is phenyl or OC(CH$_3$)$_3$;
X, Y and n are as defined above for the compound of general formula (III);
W is NR[4]R[5].A or

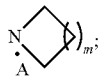

R[4], R[5] and m are as defined above for the compound of general formula (III); and
A is a pharmaceutically acceptable acid.

According to an embodiment of the present invention, in general formula (I-1),
R[1] is H, R[2] is acetyl, and R[3] is phenyl,
R[1] is H, R[2] is H, and R[3] is OC(CH$_3$)$_3$; or
R[1] is methyl, R[2] is methyl, and R[3] is OC(CH$_3$)$_3$.

According to an embodiment of the present invention, in general formula (I-2),
R[2] is acetyl and R[3] is OC(CH$_3$)$_3$.

According to an embodiment of the present invention, in general formula (I-3),
R[3] is OC(CH$_3$)$_3$.

According to an embodiment of the present invention, X is H, methyl or F.

According to an embodiment of the present invention, Y is F, CF$_3$ or CHF$_2$.

According to an embodiment of the present invention, R[4], R[5] are each independently H, methyl, ethyl, propyl, isopropyl, butyl, isobutyl, benzyl, cyclopropyl, cyclobutyl, cyclopentyl or cyclohexyl.

According to an embodiment of the present invention, X is H, methyl or F; Y is F, CF$_3$ or CHF$_2$; R[4], R[5] are each independently H, methyl, ethyl, propyl, isopropyl, butyl, isobutyl, benzyl, cyclopropyl, cyclobutyl, cyclopentyl or cyclohexyl.

According to an embodiment of the present invention, A is hydrochloric acid, hydrobromic acid, sulfuric acid, phosphoric acid, carbonic acid, acetic acid, propionic acid, methanesulfonic acid, lactic acid, benzensulfonic acid, p-toluene sulfonic acid, succinic acid, maleic acid, fumaric acid, tartaric acid, citric acid or malic acid.

According to an embodiment of the present invention, when X and Y are different (i.e., the α-C atom of the 2'-ester carbonyl in the water soluble taxane derivative is a chiral atom), the carbon atom to which both X and Y are attached is in a single R configuration, in a single S configuration, or in both R and S configurations.

According to an embodiment of the present invention, the water soluble taxane derivative is selected from the group consisting of:
2'-O-[4-N,N-dimethylamino-2(R)-fluorobutyryl]paclitaxel hydrochloride;
2'-O-[4-N,N-dimethylamino-2(R)-fluorobutyryl]paclitaxel methanesulfonate;
2'-O-[4-N,N-dimethylamino-2(R,S)-fluorobutyryl]paclitaxel hydrochloride;
2'-O-[4-N,N-dimethylamino-2(R,S)-difluoromethylbutyryl]paclitaxel citrate;
2'-O-[4-N,N-dimethylamino-2(R)-fluorobutyryl]docetaxel hydrochloride;
2'-O-[4-N,N-dimethylamino-2(R)-fluorobutyryl]docetaxel methanesulfonate;
2'-O-[4-amino-2(R,S)-trifluoromethylbutyryl]docetaxel methanesulfonate;
2'-O-[4-N,N-dimethylamino-2(R,S)-fluorobutyryl]cabazitaxel hydrochloride;
2'-O-[4-N,N-dimethylamino-2(R)-fluorobutyryl]larotaxel hydrochloride;
2'-O-[4-N,N-dimethylamino-2(R)-fluorobutyryl]tesetaxel hydrochloride;
2'-O-[4-N,N-dimethylamino-2(S)-fluorobutyryl]paclitaxel hydrochloride;
2'-O-[4-N,N-dimethylamino-2(S)-fluorobutyryl]docetaxel hydrochloride;
2'-O-[4-N,N-dimethylamino-2(R,S)-fluorobutyryl]docetaxel hydrochloride;
2'-O-[4-N,N-dimethylamino-2(R)-fluorobutyryl]cabazitaxel hydrochloride;
2'-O-[4-N,N-dimethylamino-2(S)-fluorobutyryl]cabazitaxel hydrochloride;
2'-O-[4-amino-2(R)-difluoromethylbutyryl]cabazitaxel sodium bisulfate salt;
2'-O-[4-N,N-diethylamino-2-methyl-2(R)-2-trifluoromethylbutyryl]cabazitaxel methanesulfonate;
2'-O-[4-N-methyl-N-ethylamino-2(R)-2-difluoroethylvaleryl]docetaxel hydrochloride;
2'-O-[4-N,N-dimethylamino-2(R)-fluorovaleryl]docetaxel methanesulfonate;
2'-O-[4-(aziridin-1-yl)amino-2,2-difluoroheptanoyl]docetaxel methanesulfonate;
2'-O-[4-N-methyl-N-cyclopentylamino-2-trifluoromethyl-2-fluorooctanoyl]paclitaxel methanesulfonate;
2'-O-[4-N,N-dimethylamino-2(R)-fluorovaleryl]larotaxel methanesulfonate;
2'-O-[4-N,N-dimethylamino-2(R)-fluorovaleryl]tesetaxel methanesulfonate;
2'-O-[4-N,N-dimethylamino-2(S)-fluorobutyryl]paclitaxel methanesulfonate;
2'-O-[4-N,N-dimethylamino-2(R,S)-fluorobutyryl]paclitaxel methanesulfonate;
2'-O-[4-N,N-dimethylamino-2(S)-fluorobutyryl]docetaxel methanesulfonate;
2'-O-[4-N,N-dimethylamino-2(R,S)-fluorobutyryl]docetaxel methanesulfonate;
2'-O-[4-N,N-dimethylamino-2(R)-fluorobutyryl]cabazitaxel methanesulfonate;
2'-O-[4-N,N-dimethylamino-2(S)-fluorobutyryl]cabazitaxel methanesulfonate;

2'-O-[4-N,N-dimethylamino-2(R,S)-fluorobutyryl]cabazitaxel methanesulfonate;
2'-O-[4-amino-2(R)-difluoromethylbutyryl]cabazitaxel sulfate;
2'-O-[4-N,N-diethylamino-2-methyl-2(R)-2-trifluoromethylbutyryl]cabazitaxel hydrochloride;
2'-O-[4-N-methyl-N-ethylamino-2(R)-2-difluoroethylvaleryl]docetaxel methanesulfonate;
2'-O-[4-N,N-dimethylamino-2(R)-fluorovaleryl]docetaxel hydrochloride;
2'-O-[4-(aziridin-1-yl)amino-2,2-difluoroheptanoyl]docetaxel hydrochloride;
2'-O-[4-N-methyl-N-cyclopentylamino-2-trifluoromethyl-2-fluorooctanoyl]paclitaxel hydrochloride;
2'-O-[4-N,N-dimethylamino-2(R)-fluorovaleryl]larotaxel hydrochloride;
2'-O-[4-N,N-dimethylamino-2(R)-fluorovaleryl]tesetaxel hydrochloride;
2'-O-[4-N-methyl-N-ethylamino-2(R)-fluorobutyryl]paclitaxel methanesulfonate;
2'-O-[4-N,N-diethylamino-2(S)-fluorobutyryl]paclitaxel fumarate;
2'-O-[4-N-methyl-N-isopropylamino-2(R,S)-fluorobutyryl]paclitaxel hydrochloride;
2'-O-[4-N,N-dimethylamino-2(R,S)-2-trifluoromethylbutyryl]paclitaxel p-toluene sulfonate;
2'-O-[4-N,N-dimethylamino-2(R,S)-2-difluoromethylbutyrvl]paclitaxel hydrochloride;
2'-O-[4-N,N-dimethylamino-2(R)-fluorovaleryl]paclitaxel maleate;
2'-O-[4-N,N-dimethylamino-2(S)-2-difluoromethylhexanoyl]paclitaxel sulfate;
2'-O-[4-N-methyl-N-ethylamino-2(R)-fluorobutyryl]docetaxel methanesulfonate;
2'-O-[4-N,N-diethylamino-2(S)-fluorobutyryl]docetaxel maleate;
2'-O-[4-N-methyl-N-isopropylamino-2(R)-fluorobutyryl]docetaxel hydrochloride;
2'-O-[4-N,N-dimethylamino-2(R)-2-trifluoromethylbutyryl]docetaxel methanesulfonate;
2'-O-[4-N,N-dimethylamino-2(R,S)-2-difluoromethylbutyrvl]docetaxel hydrochloride;
2'-O-[4-N,N-dimethylamino-2(R,S)-fluorovaleryl]docetaxel methanesulfonate;
2'-O-[4-N,N-dimethylamino-2(S)-fluorohexanoyl]docetaxel sulfate;
2'-O-[4-N-methyl-N-ethylamino-2(R)-fluorobutyryl]cabazitaxel maleate;
2'-O-[4-N,N-diethylamino-2(R)-fluorobutyryl]cabazitaxel methanesulfonate;
2'-O-[4-N-methyl-N-isopropylamino-2(R)-fluorobutyryl]cabazitaxel hydrochloride;
2'-O-[4-N,N-dimethylamino-2(R)-2-trifluoromethylbutyryl]cabazitaxel methanesulfonate;
2'-O-[4-N,N-dimethylamino-2(R)-2-difluoromethylbutyryl]cabazitaxel p-toluene sulfonate;
2'-O-[4-N,N-dimethylamino-2(R)-fluorovaleryl]cabazitaxel hydrochloride;
2'-O-[4-N,N-dimethylamino-2(R)-fluorohexanoyl]cabazitaxel sulfate;
2'-O-[4-N-methyl-N-ethylamino-2(R,S)-fluorobutyryl]larotaxel hydrochloride;
2'-O-[4-N-methyl-N-isopropylamino-2(R,S)-2-trifluoromethylbutyryl]larotaxel maleate;
2'-O-[4-N,N-dimethylamino-2(S)-fluorovaleryl]larotaxel phosphate;
2'-O-[4-N,N-diethylamino-2(S)-fluorobutyryl]tesetaxel hydrochloride;
2'-O-[4-N-methyl-N-isopropylamino-2(R,S)-2-trifluoromethylbutyryl]tesetaxel succinate;
2'-O-[4-(pyrrolidin-1-yl)amino-2(R,S)-fluorovaleryl]tesetaxel sulfate;
2'-O-[4-N,N-diethylamino-2(R)-fluorobutyryl]paclitaxel hydrochloride;
2'-O-[3-N,N-dimethylamino-2(R,S)-fluoropropionyl]paclitaxel hydrochloride;
2'-O-[4-N-benzylamino-2(S)-fluorobutyryl]docetaxel hydrochloride;
2'-O-[3-(N,N-diethyl)amino-2(R,S)-trifluoromethyl propionyl]docetaxel hydrochloride;
2'-O-[4-(N-methyl)amino-2(R)-trifluoromethylbutyryl]paclitaxel hydrochloride;
2'-O-[3-(N-isopropyl)amino-2(R,S)-difluoromethylpropionyl]cabazitaxel hydrochloride;
2'-O-[5-(N,N-dimethyl)amino-2(R)-fluorovaleryl]paclitaxel hydrochloride;
2'-O-[4-(N,N-dimethyl)amino-2(S)-trifluoromethylbutyryl]cabazitaxel hydrochloride;
2'-O-[4-(N-isopropyl)amino-2(R,S)-trifluoromethylbutyryl]paclitaxel hydrochloride;
2'-O-[5-N,N-dimethylamino-2(S)-trifluoromethylvaleryl]docetaxel hydrochloride;
2'-O-[4-N-benzylamino-2-methyl-2(R,S)-fluorobutyryl]paclitaxel hydrochloride;
2'-O-[4-N,N-dimethylamino-2(R)-difluoromethylbutyryl]docetaxel hydrochloride;
2'-O-[3-cyclopentylamino-2-ethyl-2(R,S)-trifluoromethylpropionyl]docetaxel hydrochloride;
2'-O-[5-N-benzylamino-2-benzyl-2(R)-difluoromethylvaleryl]cabazitaxel hydrochloride;
2'-O-[4-(4-piperidin-1-yl)-2(S)-trifluoromethylbutyryl]cabazitaxel hydrochloride;
2'-O-[4-N,N-dimethylamino-2(S)-fluorobutyryl]larotaxel hydrochloride;
2'-O-[4-N,N-dimethylamino-2(R)-fluorobutyryl]tesetaxel hydrochloride.

DETAILED DESCRIPTIONS OF THE INVENTION

Definitions

The term "$C_{1-6}$alkyl" as used herein refers to a saturated, linear or branched hydrocarbon group having 1-6 carbon atoms, such as methyl, ethyl, propyl, isopropyl, n-butyl, isobutyl, sec-butyl, tert-butyl, n-pentyl, isopentyl, neo-pentyl, n-hexyl, isohexyl and the like, preferably methyl, ethyl, propyl, isopropyl, butyl or isobutyl, more preferably methyl, ethyl or propyl.

The term "$C_{3-6}$ cycloalkyl" as used herein refers to a saturated monocyclic hydrocarbon group having 3-6 carbon atoms, such as cyclopropyl, cyclobutyl, cyclopentyl or cyclohexyl.

The term "an acid which can form a salt with an amine" as used herein refers to an inorganic or organic acid commonly used in the field of organic chemistry which can form a salt with an amine. The inorganic acid includes, but is not limited to, hydrochloric acid, hydrobromic acid, hydroiodic acid, sulfuric acid, pyrosulfuric acid, phosphoric acid, nitric acid and the like. The organic acid includes, but is not limited to, formic acid, acetic acid, propionic acid, butyric acid, pivalic acid, trifluoroacetic acid, difluoroacetic acid, fluoroacetic acid, acetoacetic acid, benzoic acid, methanesulfonic acid, ethanesulfonic acid, trifluoromethanesulfonic acid, benzensulfonic acid, p-toluene sulfonic acid, naphthalenesulfonic acid, camphorsulfonic acid, and the like.

The term "pharmaceutically acceptable acid" as used herein refers to an acid which can be used in the medical field, such as hydrochloric acid, hydrobromic acid, sulfuric acid, phosphoric acid, carbonic acid, acetic acid, propionic acid, methanesulfonic acid, lactic acid, benzensulfonic acid, p-toluene sulfonic acid, succinic acid, maleic acid, fumaric acid, tartaric acid, citric acid or malic acid.

Reaction Scheme

Compound (I-1) of the present invention can be prepared according to following Reaction Scheme 1:

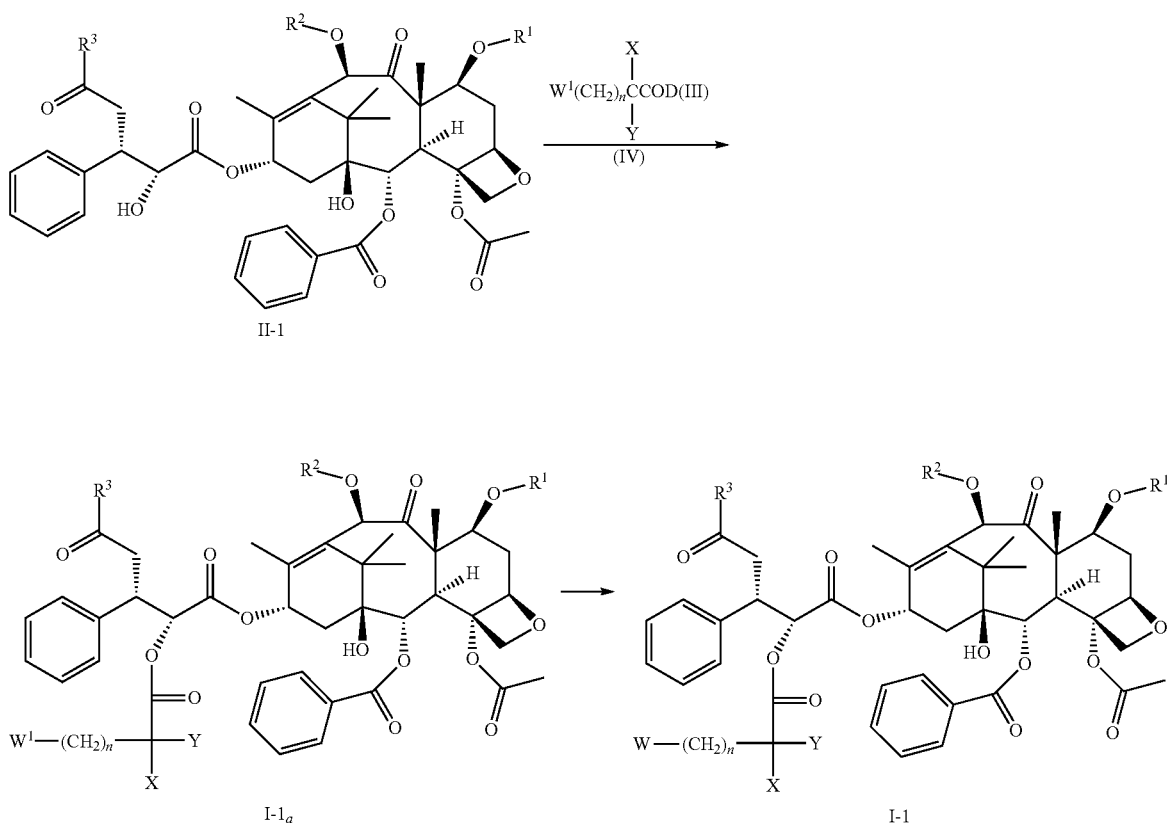

Compound (I-2) of the present invention can be prepared according to following Reaction Scheme 2:

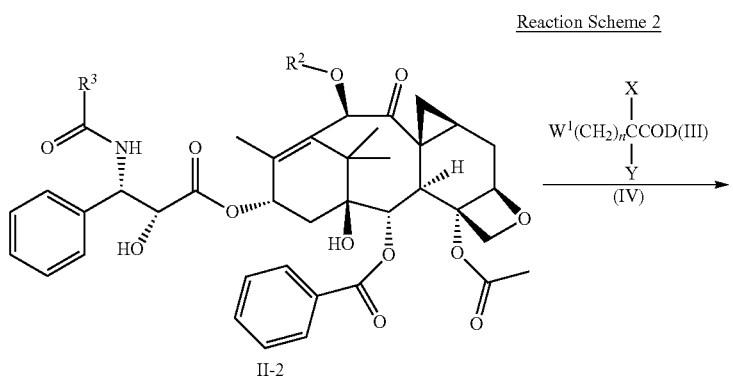

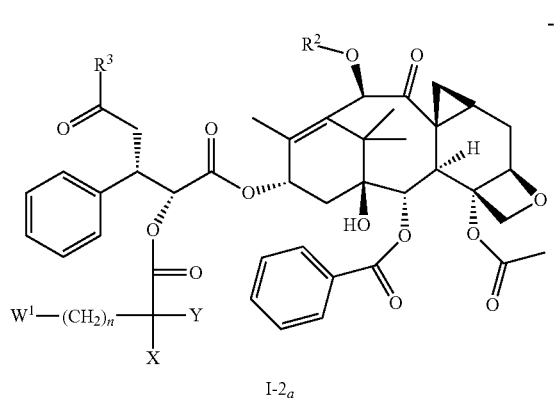

I-2a

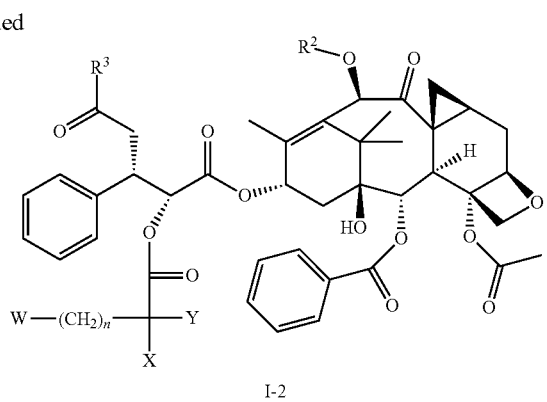

I-2

Compound (I-3) of the present invention can be prepared according to following Reaction Scheme 3:

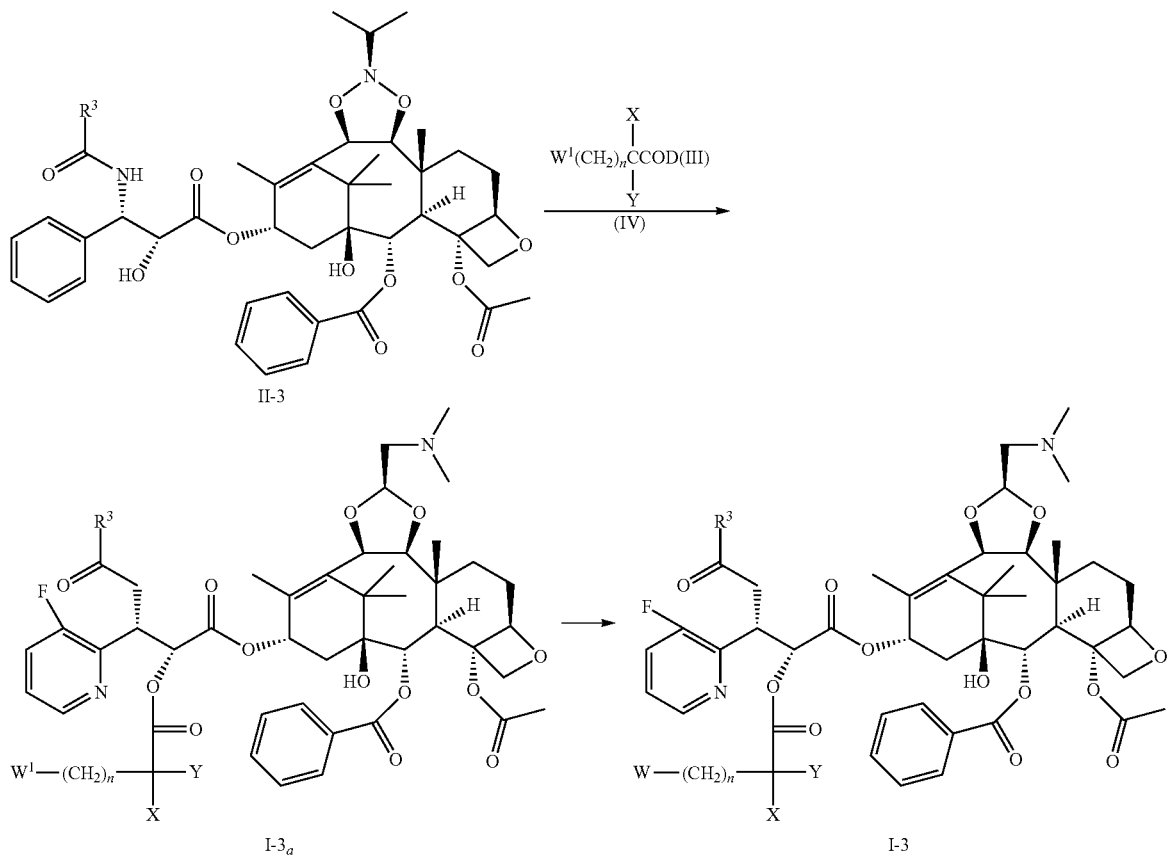

wherein $R^1$, $R^2$, $R^3$, X, Y, n, W, $W^1$ and D are as defined above.

Step 1

The compound of general formula I-1a, I-2a or I-3a is prepared by reacting the compound of general formula II-1, II-2 or II-3 with the compound of general formula (III), respectively, in the presence of reagent (IV) at −100-40° C.

Step 2

The compound of general formula I-1 or I-2 is prepared by dissolving the corresponding compound of general formula I-1a or I-2a in an organic solvent, and then washing the organic layer with a saturated aqueous solution of a salt of acid A which is adjusted to below pH 5 with acid A; or the compound of general formula I-3 is prepared by dissolving the corresponding compound of general formula I-3a in an organic solvent, and then washing the organic layer with a saturated aqueous solution of a salt of acid A which is adjusted to below pH 6 with acid A.

The organic solvent mentioned above refers to an aprotic organic solvent which can dissolve the compound of general formula I-1a, I-2a or I-3a, e.g., dichloromethane, chloroform, 1,2-dichloroethane, chlorobenzene, acetonitrile and the like.

The reagent (IV) mentioned above is a nitrogen-containing basic organic reagent or a mixed reagent consisting of a nitrogen-containing basic organic reagent and a compound having a carbodiimide structure. The nitrogen-containing basic organic reagent is an organic base, such as triethylamine, pyridine, DMAP (4-N,N-dimethylaminopyridine) or 4-PPY (4-pyrrolidinylpyridine); and the compound having a carbodiimide structure is DCC (dicyclohexylcarbodiimide) or EDC (1-(3-dimethylaminopropyl)-3-ethylcarbodiimide).

When D in the compound of general formula (III) is Cl or Br, the reagent (IV) is a nitrogen-containing basic organic reagent, and the molar ratio of the compound of general formula (II) (i.e., the compound of II-1, II-2 or II-3), the compound of general formula (III) and reagent (IV). i.e., (II):(III):(IV), is 1:(1-12.0):(1-15.0).

When D in the compound of general formula (III) is OH, the reagent (IV) is a mixed reagent consisting of a nitrogen-containing basic organic reagent and a compound having a carbodiimide structure in a molar ratio of 1:(1-5), and the molar ratio of the compound of general formula (II) (i.e., the compound of II-1, II-2 or II-3), the compound of general formula (III) and the reagent (IV), i.e., (II):(III):(IV) is 1:(1-12.0):(1-15.0) (wherein the amount of the reagent (IV) is based on the amount of the nitrogen-containing basic organic reagent).

Specifically, the present invention provides a method for preparing a water soluble taxane derivative. The method comprises: dissolving a pharmaceutically active taxane compound (II-1, II-2 or II-3) in dichloromethane in the presence of pyridine or DMAP at −50° C.-50° C., slowly adding a solution of the compound of general formula (III) in dichloromethane dropwise, conducting separation after completion of the reaction, dissolving the product thus obtained in dichloromethane, and washing the organic layer with a saturated aqueous solution of a salt of acid A which is adjusted to an appropriate pH with acid A to obtain a water soluble taxane derivative of the present invention. The molar ratio of the pharmaceutically active taxane compound, the derivative of amino acid and pyridine or DMAP is 1:(1-10):(3-10.0).

The carboxylic acid derivative of general formula (III) of the present invention can be prepared according to following Reaction Scheme 4:

In the above Reaction Scheme 4, the compounds of formulae (IIIa), (IIIb) and (IIIc), which all belong to the compound of general formula (III), are obtained by reacting the compound of general formula (V) with an alkylating agent for amino ($C_1$ or $C_3$) or a protecting agent for amino ($C_2$), wherein, $R^4$, X, Y, n and B are as defined above;

$C_1$ is an alkylating agent for amino, such as formic acid/formaldehyde, dimethyl sulfate, bromoethane, bromopropane, chlorobutane, acetone, butanone, cyclopentanone, cyclohexanone, benzaldehyde and the like;

$C_2$ is a protecting agent for amino, such as benzyl chloroformate, di-tert-butyloxycarbonylcarbonic anhydride, benzyl chloride, benzyl bromide and the like;

$C_3$ is another alkylating agent for amino, such as 1-chloro-2-bromoethane, 1-chloro-4-bromobutane, 1-chloro-5-bromopentane and the like;

$R^{5a}$ is alkyl or cycloalkyl, especially $C_{1-6}$ alkyl, such as methyl, ethyl, propyl, isopropyl, butyl or isobutyl, or $C_{3-6}$ cycloalkyl, such as cyclopropyl, cyclobutyl, cyclopentyl or cyclohexyl.

$R^{5b}$ is an amino protecting group, especially $C_{1-6}$ alkoxycarbonyl optionally substituted with phenyl (such as benzyloxycarbonyl or tert-butyloxycarbonyl) or benzyl.

When D in the compound of general formula (III) is Cl or Br, a corresponding acyl halide compound can be prepared from a starting material wherein D is hydroxyl via a halogenating reaction with a halogenating reagent (such as thionyl chloride, phosphorus trichloride, phosphorous pentachloride or phosphorus tribromide).

The compound of general formula (V) in the above reaction schemes can be obtained by methods reported in relevant references, e.g. [1] Chencomm, 1999: 1739-1740; [2] J. Med. Chem, 2011, 44:2849-2856; [3] JCS Perkin I 1980: 2029-2032; [4] Journal of Fluorine Chemistry (23), 1983: 241-259; [5] Journal of Fluorine Chemistry, 2004, vol. 125 (4): 509-515.

Use of the Water Soluble Taxane Derivative of the Present Invention in the Preparation of an Antitumor Drug The water soluble taxane derivative of the present invention, as a prodrug, has the following beneficial effects:

The water soluble taxane derivative of general formula I-1, I-2 or I-3 of the present invention has higher water solubility than the corresponding compound of general formula II-1, II-2 or II-3, and thus can be formulated as a water soluble injection. After intravenous injection into an animal body, it can release the corresponding parent drug, so as to inhibit the growth of tumors.

The inventors prepare an ester derivative of a taxane drug through structural modification without changing the pharmacological activity of the parent drug, and form a salt thereof with a corresponding acid to facilitate dissociation in vivo. The water soluble taxane derivative of the present invention is relatively stable in chemical properties, and the aqueous solution thereof can release the parent drug after injection, thus overcoming the following disadvantages of currently available taxane preparations caused by the presence of polyethoxylated castor oil or Tween-80: acute hypersensitivity, neurotoxicity, liver toxicity, etc. In addition, the preparation method of the present invention is simple and safe to perform, and the quality of the product can be easily controlled.

Reaction Scheme 4

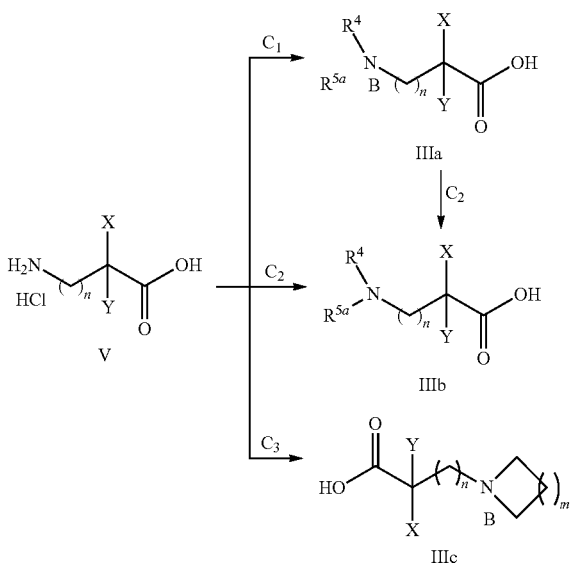

EXAMPLES

To make the purpose and technical solutions of the present invention more clear, the preferable examples of the present invention are described in more detail as follows. It should be noted that the following examples are provided merely for further illustration of the present invention, but should not be construed to limit the scope of the present invention. Technical solutions obtained through non-essential improvements and adjustments by a person skilled in the art according to the above disclosure of the present invention all belong to the protection scope of the present invention, A. Preparation of the Carboxylic Acid Derivative of General Formula (III) of the Present Invention Example 1

Preparation of 4-N,N-dimethylamino-2(R)-fluorobutyric acid hydrochloride 4-amino-2(R)-fluorobutyric acid hydrochloride (1.1 g, 7.0 mmol) was added to a round bottom flask, a saturated aqueous $Na_2CO_3$ solution was added to adjust the pH value to 8, and then 88% formic acid (6 ml) and 35% aqueous formaldehyde solution (5 ml) were added. The reaction mixture was warmed slowly to 80° C., and was allowed to react for 15 hours. The reaction mixture was cooled to room temperature, and 6 N hydrochloric acid (2 ml) was added followed by concentration under reduced pressure to give a light yellow solid. The solid was dissolved in methanol (10 ml), and the resulting solution was cooled in an ice bath with stirring for 30 min. Then the resulting mixture was filtered, and the filtrate was concentrated. The residue was refluxed in 6 N hydrochloric acid (100 ml) for 4 hours, and the liquid was removed by rotary evaporation. The solid thus obtained was treated with acetonitrile to obtain a white solid (1.1 g, yield: 85%).

m.p.: 136-138° C.:
$^1$H-NMR (400 MHz, $D_2O$): δ 4 72 (ddd, 1H), 2.90 (dtd, 2H), 2.43 (s, 6H), 1.93 (m, 2H);
$^{13}$C-NMR (600 MHz, $D_2O$): δ 173.13, 86.90, 53.49, 42.83, 26.91;
ESI-MS m/z $[M+H]^+$ 150.13.

Example 2

Preparation of 4-N-isopropylamino-2(R,S)-fluorobutyric acid hydrochloride 4-amino-2(R,S)-fluorobutyric acid hydrochloride (1.1 g, 7.0 mmol) was added to a round bottom flask (50 ml), a saturated aqueous $Na_2CO_1$ solution was added to adjust the pH to 8, and then acetone (15 ml) and 5% Pd—C (100 mg) were added. Air was replaced with nitrogen, which was then replaced with hydrogen. The reaction was carried out for 6 hours at room temperature. Pd—C was removed through filtration, and the pH of the solution was adjusted to acidic with 6 N hydrochloric acid. The solution was concentrated under reduced pressure to give a light yellow solid. The solid was dissolved in methanol (10 ml), and the resulting solution was cooled in an ice bath with stirring for 30 min. Then the resulting mixture was filtered, and the filtrate was concentrated. The residue was refluxed in 6 N hydrochloric acid (100 ml) for 4 hours, and the solvent was removed by rotary evaporation. The solid thus obtained was treated with acetonitrile to obtain a white solid (1.05 g, yield: 75%).

ESI-MS m/z $[M+H]^+$ 164.12.

Example 3

Preparation of 4-N,N-diethylamino-2(R,S)-trifluoromethylbutyric acid hydrochloride 4-amino-2(R,S)-trifluoromethylbutyric acid hydrochloride (2.07 g, 10 mmol) was added to a round bottom flask (50 ml), and 1 N aqueous $NaHCO_3$ solution was added to adjust the pH value to 8. Acetonitrile (50 ml) was added, and a mixed solution (10 ml) of bromoethane (2.18 g, 20 mmol) and acetonitrile was added dropwise. The pH of the reaction solution was maintained at 7-8 with a solution of sodium bicarbonate. Hydrochloric acid was added to adjust the pH to below 5 after completion of the reaction, and the solution was concentrated under reduced pressure to give a light yellow solid. Methanol (10 ml) was added, the resulting solution was stirred for 30 min before filtration, and the filtrate was concentrated. The residue was refluxed in 6 N hydrochloric acid (100 ml) for 4 hours, the solvent was removed by rotary evaporation, and a white solid (yield: 130/0) was obtained.

ESI-MS m/z $[M+H]^+$ 228.16.

Example 4

Preparation of 4-N-benzylamino-2,2-difluorobutyric acid hydrochloride

The title compound was prepared according to the method of Example 2, using 4-amino-2,2-difluorobutyric acid hydrochloride (1.1 g, 5.6 mmol) and benzaldehyde as starting materials.

ESI-MS nm/z $[M+H]^+$ 230.06.

Example 5

Preparation of 4-N-isobutylamino-2(R,S)-difluoromethylbutyric acid hydrochloride The title compound was prepared according to the method of Example 2, using 4-amino-2(R,S)-difluoromethylbutyric acid hydrochloride (1.90 g, 10 mmol) and butanone (15 ml) as starting materials, and a white solid (1.1 g, yield: 45%) was obtained.

m.p.: 141-142° C.;
ESI-MS m/z $[M+H]^+$ 210.1.

Example 6

Preparation of 4-N-(aziridin-1-yl)-2(R,S)-difluoromethylbutyric acid hydrochloride 4-amino-2(R,S)-difluoromethylbutyric acid hydrochloride (1.90 g, 10 mmol) was added to a round bottom flask (50 ml), an aqueous $NaHCO_3$ solution was added to adjust the pH to 7-8, and acetonitrile (15 ml) and 1-chloro-2-bromoethane (10 mmol) were added. The reaction was carried out at ambient temperature for 0.5 h, and then the reaction mixture was heated to reflux and was allowed to react under reflux for 2 h. The solvent was removed by evaporation under reduced pressure, and methanol (10 ml) was added to the residue. The resulting solution was then cooled in an ice bath with stirring for 30 min before filtration, and the filtrate was concentrated. The residue was refluxed in 6 N hydrochloric acid (100 ml) for 4 hours, the solvent was removed by rotary evaporation, and a white solid (0.7 g) was obtained.

ESI-MS m/z [M+H]$^+$ 180.14.

Example 7

Preparation of 4-N-(pyrrolidin-1-yl)-2(R,S)-fluorobutyric acid hydrochloride

The title compound was prepared according to the method of Example 6, using 4-amino-2(R,S)-fluorobutyric acid and 1-chloro-4-bromobutane as starting materials.

ESI-MS m/z [M+H]$^+$ 176.1.

Example 8

Preparation of 3-N-benzylamino-2(R,S)-(1,1-difluoromethyl)propionic acid hydrochloride The title compound was prepared according to the method of Example 2, using 3-amino-2(R,S)-(1,1-difluoromethyl) propionic acid hydrochloride and benzaldehyde as starting materials.

ESI-MS m/z [M+H]$^+$ 230.19.

Example 9

Preparation of 6-N-cyclohexylamino-2(R,S)-trifluoromethylhexanoic acid hydrochloride The title compound was prepared according to the method of Example 2, using 6-amino-2(R,S)-trifluoromethylhexanoic acid hydrochloride and cyclohexanone as starting materials.

ESI-MS m/z [M+H]$^+$ 282.08.

According to the above examples, the inventors also prepared the following compounds:
sodium 4-N,N-dimethylamino-2(R,S)-fluorobutyrate (ESI-MS m/z [M−H] 149.03);
calcium 4-N,N-diethylamino-2(R,S)-fluorobutyrate (ESI-MS m/z [M−H] 177.08);
aluminum 3-N-benzylamino-2(R,S)-benzyloxypropionate (ESI-MS m/z [M−H] 197.04);
4-N,N-dimethylamino-2(R,S)-fluorobutyryl chloride hydrochloride (ESI-MS m/z [M−H] 168.01);
4-N-benzylamino-2,2-difluorobutyryl chloride hydrochloride (ESI-MS m/z [M−H] 248.03);
4-N,N-dimethylamino-2(R,S)-fluorobutyric acid (ESI-MS m/z [M−H] 150.08); and
4-N,N-dimethylamino-2(S)-fluorobutyric acid hydrochloride (ESI-MS m/z [M−H] 150.11).

B. Preparation of the Water Soluble Taxane Derivative of the Present Invention

B-1. Preparation of Paclitaxel Derivatives

Example 10

2'-O-[4-N,N-dimethylamino-2(R)-fluorobutyryl] paclitaxel hydrochloride (compound O1)

1) The preparation of 4-N,N-dimethylamino-2(R)-fluorobutyryl chloride hydrochloride: 4-N,N-dimethylamino-2 (R)-fluorobutyric acid hydrochloride (10 mmol) was placed in thionyl chloride (10 ml) in a flask, the mixture was slowly warmed to 40° C., and the reaction was carried out for 4 h. Thionyl chloride was evaporated under reduced pressure, and anhydrous dichloromethane (15 ml) was added. The solvent was evaporated under reduced pressure, and anhydrous dichloromethane (60 ml) was added to the residue to obtain a solution for the next step.

2) At −50° C., paclitaxel (1.6 g) and 4-N,N-dimethylaminopyridine (1.4 g) were added to dichloromethane (DCM, 150 ml), and the mixture was stirred to dissolve. The solution of 4-N,N-dimethylamino-2(R)-fluorobutyryl chloride hydrochloride in dichloromethane prepared in step 1) was slowly added dropwise, and the reaction was detected by HPLC. Upon completion of the reaction, the DCM layer was washed with a saturated aqueous sodium chloride solution (the pH of which was adjusted to about 3.0 with hydrochloric acid), dried over anhydrous sodium sulfate, and filtered. DCM was removed by rotary evaporation, and the residue was crystallized from acetone and methyl tert-butyl ether to obtain a white solid (yield: 50%).

ESI-MS m/z [M+H]$^+$: 985.4.

$^1$H-NMR (400 MHz, DMSO): δ 7.86 (m, 2H), 7.79 (m, 2H), 7.68 (t, 1H), 7.59 (m, 3H), 7.48 (t, 2H), 7.38 (m, 2H), 7.25 (m, 3H), 6.18 (s, 1H), 6.15 (s, 1H), 5.79 (s, 1H), 4.98 (t, 2H), 4.85 (d, J=6.24 Hz, 1H), 4.26 (d, 1H), 3.72 (d, J=7.62 Hz, 1H), 3.64 (t, 1H), 2.89 (t, 2H), 2.54 (s, 1H), 2.26 (t, 2H), 2.18 (m, 13H), 2.01 (s, 3H), 1.95 (m, 2H), 1.86 (m, 1H), 1.75 (m, 1H), 1.68 (m, 1H), 1.52 (s, 6H), 1.41 (s, 3H).

$^{13}$C-NMR (600 MHz, DMSO): δ=203.64, 171.32, 170.65, 169.63, 168.96, 165.98, 165.86, 140.36, 140.21, 137.12, 134.65, 134.12, 133.98, 133.89, 133.21, 130.65, 129.94, 128.98, 128.54, 128.43, 128.12, 85.12, 81.45, 80.65, 78.23, 76.58, 76.46, 76.45, 74.98, 72.56, 70.23, 59.64, 54.87, 53.03, 48.65, 43.45, 42.26, 42.15, 41.96, 38.96, 34.45, 28.20, 23.97, 21.65, 21.01, 11.23.

Example 11

2'-O-[4-N,N-dimethylamino-2(R)-fluorobutyryl] paclitaxel methanesulfonate (compound C1)

The hydrochloride salt prepared in Example 10 was dissolved in DCM (25 ml), and the solution was washed with a solution of sodium methanesulfonate (above 1 mol/L, pH=3, the pH value was adjusted with methanesulfonic acid) (15 ml*4). The organic layer was dried over anhydrous sodium sulfate and filtered, and the solvent was removed through evaporation under reduced pressure. The residue was crystallized from acetone and methyl tert-butyl ether to give a white solid (yield: 53%).

Example 12

2'-O-[4-N,N-dimethylamino-2(R,S)-fluorobutyryl] paclitaxel hydrochloride (compound 03)

At −50° C., paclitaxel (2 g) and 4-N,N-dimethylaminopyridine (1.9 g) were added to dichloromethane (DCM, 150 ml), and the mixture was stirred to dissolve. The reaction was detected by HPLC. A 3% solution of 4-N,N-dimethylamino-2(R,S)-fluorobutyryl chloride hydrochloride (prepared according to Example 10.1, using 4-N,N-dimethylamino-2(R,S)-fluorobutyric acid hydrochloride as a starting material) in dichloromethane was slowly added dropwise, and the reaction was detected by HPLC. Upon completion of the reaction, the DCM layer was washed with a saturated aqueous sodium chloride solution (the pH of which was adjusted to about 3.0 with hydrochloric acid), dried over anhydrous sodium sulfate, and filtered, and DCM was removed by rotary evaporation. The residue was crystallized from acetone and methyl tert-butyl ether to give a white solid (yield: 48%).

ESI-MS m/z [M+H]$^+$: 985.4.

Example 13

2'-O-[4-N,N-dimethylamino-2(R,S)-difluoromethyl-butyryl]paclitaxel citrate (C92)

At −50° C., 4-(N,N-dimethyl)amino-2(R,S)-difluoromethylbutyric acid hydrochloride (2.0 g), 4-N,N-dimethylaminopyridine (1.8 g), and dicyclohexylcarbodiimide (2.1 g) were added to acetonitrile (150 ml). Paclitaxel (1.6 g) was added, and the reaction was carried out for 18 hours. Upon completion of the reaction, the solvent was removed by evaporation under reduced pressure, and the residue was dissolved in dichloromethane (100 ml). The DCM layer was washed with a saturated aqueous sodium chloride solution (the pH of which was adjusted to about 3.0 with hydrochloric acid), dried over anhydrous sodium sulfate, and filtered. DCM was removed by rotary evaporation, and the residue was dissolved in a little acetone. Isopropyl ether was added for crystallization, and 2'-O-[4-N,N-dimethylamino-2(R,S)-difluoromethylbutyryl]paclitaxel hydrochloride (1.2 g) was obtained. The hydrochloride salt was dissolved in dichloromethane (100 ml). The dichloromethane layer was washed with an aqueous solution (pH=3) of citric acid and sodium citrate, dried over anhydrous sodium sulfate, and filtered. The solvent was removed by rotary evaporation, and 2'-O-[4-N,N-dimethylamino-2(R,S)-difluoromethylbutyryl] paclitaxel citrate (1.05 g) was obtained.

ESI-MS m/z [M+H]$^+$: 1017.54.

B-2. Preparation of Docetaxel Derivatives

Example 14

2'-O-[4-N,N-dimethylamino-2(R)-fluorobutyryl] docetaxel hydrochloride (compound 04)

At −15° C., docetaxel (2.1 g) and 4-N,N-dimethylaminopyridine (1.8 g) were added to dichloromethane (DCM, 150 ml), and the mixture was stirred to dissolve. A solution of 4-N,N-dimethylamino-2(R)-fluorobutyryl chloride hydrochloride (prepared according to Example 10.1, using 4-N,N-dimethylamino-2(R)-fluorobutyric acid hydrochloride as a starting material) in dichloromethane was slowly added dropwise, and the reaction was monitored by HPLC. Upon completion of the reaction, the DCM layer was washed with a saturated aqueous sodium chloride solution (the pH of which was adjusted to about 3.0 with hydrochloric acid), dried over anhydrous sodium sulfate, and filtered. DCM was removed by rotary evaporation, and the residue was crystallized from acetone and methyl tert-butyl ether to give a white solid (yield: 51%).

ESI-MS m/z [M+H]$^+$: 939.54.

$^1$H-NMR (400 MHz, DMSO): δ 7.93 (dd, 2H), 7.64 (dt, 1H), 7.40 (m, 2H), 7.19 (d, J=6.42 Hz, 2H), 5.82 (s, 3H), 5.38 (m, 1H), 5.33 (m, 1H), 5.23 (d, J=7.64 Hz, 2H), 5.13 (m, 1H), 5.00 (d, J=5.23 Hz 1H), 4.89 (m, 1H), 4.44 (s, 1H), 4.00 (s, 3H), 3.63 (d, J=7.17 Hz, 2H), 2.59 (dd, 1H), 2.45 (s, 1H), 2.43 (m, 3H), 2.14 (m, 6H), 2.06 (m, 5H), 1.88 (s, 3H), 1.61 (m, 1H), 1.33 (s, 1H), 1.14 (m, 7H), 0.97 (s, 15H), 0.82 (t, 3H).

$^{13}$C-NMR (600 MHz, DMSO): δ 209.458, 169.376, 168.425, 167.682, 167.513, 166.869, 165.229, 155.167, 137.026, 136.896, 135.884, 133.171, 131.278, 129.960, 129.539, 128.542, 128.044, 127.201, 86.406, 85.187, 83.701, 80.367, 79.033, 78.811, 78.596, 76.788, 75.416, 74.703, 73.715, 71.883, 70.710, 67.308, 57.007, 54.708, 51.949, 45.925, 42.867, 42.515, 42.086, 39.909, 39.771, 39.625, 39.488, 39.350, 39.212, 39.074, 38.077, 36.391, 34.675, 29.777, 28.980, 28.337, 28.061, 26.566, 26.436, 26.298, 23.209, 22.405, 20.627, 13.806, 13.614, 10.717, 9667.

Example 15

2'-O-[4-N,N-dimethylamino-2(R)-fluorobutyryl] docetaxel methanesulfonate (compound C4)

The hydrochloride salt prepared in Example 14 was dissolved in DCM (25 ml), which was washed with a solution of sodium methanesulfonate (above 1 mol/L, pH=3, the pH value was adjusted with methanesulfonic acid) (15 ml×4) The organic layer was dried over anhydrous sodium sulfate, and filtered. The solvent was removed through evaporation under reduced pressure, and the residue was crystallized from acetone and methyl tert-butyl ether to give a white solid (yield: 47%).

Example 16

2'-O-[4-amino-2(R,S)-trifluoromethylbutyryl]docetaxel methanesulfonate (C59)

At −60° C., docetaxel (1.4 g) and 4-N,N-dimethylpyridine (1.2 g) were added to dichloromethane (150 ml), and the mixture was stirred to dissolve. The reaction was detected by HPLC. A 5% solution of 4-N,N-dibenzylamino-2(R,S)-trifluoromethylbutyryl chloride hydrochloride (prepared according to Example 10.1, using 4-N,N-dibenzylamino-2(R,S)-trifluoromethylbutyric acid hydrochloride as a starting material) in dichloromethane was slowly added dropwise, and a solid (1.25 g) was obtained according to the procedures in Example 10. The obtained solid was hydrogenolysis under the catalysis of Pd/C to remove benzyl, and a solid (1.1 g) was obtained, which was dissolved in dichloromethane (100 ml). The dichloromethane layer was washed with an aqueous solution (pH=3) of methanesulfonic acid and sodium methanesulfonate, dried over anhydrous sodium sulfate, and filtered. The solvent was removed by rotary evaporation, and 2'-O-[4-amino-2(R,S)-trifluoromethylbutyryl]docetaxel methanesulfonate (950 mg) was obtained.

ESI-MS m/z [M+H]$^+$: 961.38.

B-3. Preparation of Cabazitaxel Derivatives

Example 17

2'-O-[4-N,N-dimethylamino-2(R,S)-fluorobutyryl] cabazitaxel hydrochloride (compound 09)

At −30° C., cabazitaxel (1.8 g) and 4-N,N-dimethylaminopyridine (1.7 g) were added to dichloromethane (DCM, 150 ml), and the mixture was stirred to dissolve. The reaction was detected by HPLC. A solution of 4-N,N-diethylamino-2(R,S)-fluorobutyryl chloride hydrochloride in dichloromethane was slowly added dropwise. A solid (1.4 g) was obtained according to the procedures in Example 4.

ESI-MS m/z [M+H]$^+$: 967.62.

$^1$H-NMR (400 MHz, DMSO): δ 7.93 (dd, 2H), 7.64 (dt, 1H), 7.40 (m, 2H), 7.19 (d, J=6.42 Hz, 2H), 5.82 (s, 3H), 5.38 (m, 1H), 5.33 (m, 1H), 5.23 (d, J=7.64 Hz, 2H), 5.13

(m, 1H), 5.00 (d, J=5.23 Hz, 1H), 4.89 (m, 1H), 4.44 (s, 1H), 4.00 (s, 3H), 3.63 (d, J=7.17 Hz, 2H), 3.44 (s, 3H), 3.58 (s, 3H), 2.59 (dd, 1H), 2.45 (s, 1H), 2.43 (m, 3H), 2.14 (m, 6H), 2.06 (m, 5H), 1.88 (s, 3H), 1.61 (m, 1H), 1.33 (s, 1H), 1.14 (m, 7H), 0.97 (s, 15H), 0.82 (t, 3H).

$^{13}$C-NMR (600 MHz, DMSO): δ 209.45, 169.37, 168.42, 167.68, 167.51, 166.87, 165.23, 155.17, 137.02, 136.89, 135.88, 133.17, 131.28, 129.96, 129.54, 128.54, 128.04, 127.20, 86.40, 85.18, 83.70, 80.36, 79.03, 78.81, 78.59, 76.78, 75.42, 74.70, 73.72, 71.88, 70.71, 67.31, 57.01, 56.48, 54.71, 51.95, 45 93, 42.87, 42.52, 42.08, 39.91, 39.77, 39.63, 39.48, 39.35, 39.21, 39.07, 38.08, 36.39, 34.68, 29.78, 28.98, 28.34, 28.06, 26.57, 26.44, 26.29, 23.21, 22.41, 20.63, 13.81, 13.61, 10.72, 9.67.

B-4. Preparation of Larotaxel Derivatives

Example 18

2'-O-[4-N,N-dimethylamino-2(R)-fluorobutyryl] larotaxel hydrochloride (compound C39)

At −20° C., larotaxel (1.3 g) and 4-N,N-dimethylaminopyridine (1.3 g) were added to dichloromethane (DCM, 150 ml), and the mixture was stirred to dissolve. The reaction was detected by HPLC. A solution of 4-N,N-dimethylamino-2(R)-fluorobutyryl chloride hydrochloride in dichloromethane was slowly added dropwise, and a solid (0.9 g) was obtained according to the procedures in Example 10.

ESI-MS m/z [M+H]$^+$: 963.40.

B-5. Preparation of tesetaxel derivatives

Example 19

2'-O-[4-N,N-dimethylamino-2(R)-fluorobutyryl] tesetaxel hydrochloride (compound C43)

At −40° C., tesetaxel (1 g) and 4-N,N-dimethylaminopyridine (0.8 g) were added to dichloromethane (DCM, 100 ml), and the mixture was stirred to dissolve. The reaction was detected by HPLC. A solution of 4-N,N-dimethylamino-2 (R)-fluorobutyryl chloride hydrochloride in dichloromethane was slowly added dropwise, and the reaction was carried out according to the procedures in Example 4. Upon completion of the reaction, the DCM layer was washed with a saturated aqueous sodium chloride solution (the pH was adjusted to about 6.0 with hydrochloric acid), dried over anhydrous sodium sulfate, and filtered. DCM was removed by rotary evaporation, and the residue was crystallized from acetone and methyl tert-butyl ether to give a white solid (0.7 g).

ESI-MS m/z [M+H]$^+$: 1013.52.

The inventors also prepared the following compounds according to the methods of the above examples:

2'-O-[4-N,N-dimethylamino-2(S)-fluorobutyryl]paclitaxel hydrochloride (Compound No. 02): ESI-MS m/z [M+H]+ 985.39

2'-O-[4-N,N-dimethylamino-2(S)-fluorobutyryl]docetaxel hydrochloride (Compound No. 05): ESI-MS m/z [M+H]+ 939.55

2'-O-[4-N,N-dimethylamino-2(R,S)-fluorobutyryl]docetaxel hydrochloride (Compound No. 06): ESI-MS m/z [M+H]+ 939.57

2'-O-[4-N,N-dimethylamino-2(R)-fluorobutyryl]cabazitaxel hydrochloride (Compound No. 07): ESI-MS m/z [M+H]+ 967.59

2'-O-[4-N,N-dimethylamino-2(S)-fluorobutyryl]cabazitaxel hydrochloride (Compound No. 08): ESI-MS m/z [M+H]+ 967.62

2'-O-[4-amino-2(R)-difluoromethylbutyryl]cabazitaxel sodium bisulfate salt (Compound No. 10): ESI-MS m/z [M+H]+ 971.41

2'-O-[4-N,N-diethylamino-2-methyl-2(R)-2-trifluoromethylbutyryl]cabazitaxel methanesulfonate (Compound No. 11): ESI-MS m/z [M+H]+ 1059.49

2'-O-[4-N-methyl-N-ethylamino-2(R)-2-difluoroethylvaleryl]docetaxel hydrochloride (Compound No. 12): ESI-MS m/z [M+H]+ 1013.45

2'-O-[4-N,N-dimethylamino-2(R)-fluorovaleryl]docetaxel methanesulfonate (Compound No. 13): ESI-MS m/z [M+H]+ 953.43

2'-O-[4-(aziridin-1-yl)amino-2,2-difluoroheptanoyl]docetaxel methanesulfonate (Compound No. 14): ESI-MS m/z [M+H]+ 997.37

2'-O-[4-N-methyl-N-cyclopentylamino-2-trifluoromethyl-2-fluorooctanoyl]paclitaxel methanesulfonate (Compound No. 15): ESI-MS m/z [M+H]+ 1163.41

2'-O-[4-N,N-dimethylamino-2(R)-fluorovaleryl]larotaxel methanesulfonate (Compound No. 16): ESI-MS m/z [M+H]+ 977.29

2'-O-[4-N,N-dimethylamino-2(R)-fluorovaleryl]tesetaxel methanesulfonate (Compound No. 17): ESI-MS m/z [M+H]+ 1027.39

2'-O-[4-N,N-dimethylamino-2(S)-fluorobutyryl]paclitaxel methanesulfonate (Compound No. C2): ESI-MS m/z [M+H]+ 985.37

2'-O-[4-N,N-dimethylamino-2(R,S)-fluorobutyryl]paclitaxel methanesulfonate (Compound No. C3): ESI-MS m/z [M+H]+ 985.41

2'-O-[4-N,N-dimethylamino-2(S)-fluorobutyryl]docetaxel methanesulfonate (Compound No. C5): ESI-MS m/z [M+H]+ 939.55

2'-O-[4-N,N-dimethylamino-2(R,S)-fluorobutyryl]docetaxel methanesulfonate (Compound No. C6): ESI-MS m/z [M+H]+ 939.56

2'-O-[4-N,N-dimethylamino-2(R)-fluorobutyryl]cabazitaxel methanesulfonate (Compound No. C7): ESI-MS m/z [M+H]+ 967.58

2'-O-[4-N,N-dimethylamino-2(S)-fluorobutyryl]cabazitaxel methanesulfonate (Compound No. C8): ESI-MS m/z [M+H]+ 967.54

2'-O-[4-N,N-dimethylamino-2(R,S)-fluorobutyryl]cabazitaxel methanesulfonate (Compound No. C9): ESI-MS m/z [M+H]+ 967.62

2'-O-[4-amino-2(R)-difluoromethylbutyryl]cabazitaxel sulfate (Compound No. C10): ESI-MS m/z [M+H]+ 971.39

2'-O-[4-N,N-diethylamino-2-methyl-2(R)-2-trifluoromethylbutyryl]cabazitaxel hydrochloride (Compound No. C11): ESI-MS m/z [M+H]+ 1059.54

2'-O-[4-N-methyl-N-ethylamino-2(R)-2-difluoroethylvaleryl]docetaxel methanesulfonate (Compound No. C12): ESI-MS m/z [M+H]+ 1013.43

2'-O-[4-N,N-dimethylamino-2(R)-fluorovaleryl]docetaxel hydrochloride (Compound No. C13): ESI-MS m/z [M+H]+ 953.41

2'-O-[4-(aziridin-1-yl)amino-2,2-difluoroheptanoyl]docetaxel hydrochloride (Compound No. C14): ESI-MS m/z [M+H]+ 997.39

2'-O-[4-N-methyl-N-cyclopentylamino-2-trifluoromethyl-2-fluorooctanoyl]paclitaxel hydrochloride (Compound No. C15): ESI-MS m/z [M+H]+ 1163.38

2'-O-[4-N,N-dimethylamino-2(R)-fluorovaleryl]larotaxel hydrochloride (Compound No. C16): ESI-MS m/z [M+H]+ 977.30

2'-O-[4-N,N-dimethylamino-2(R)-fluorovaleryl]tesetaxel hydrochloride (Compound No. C17): ESI-MS m/z [M+H]+ 1027.36

2'-O-[4-N-methyl-N-ethylamino-2(R)-fluorobutyryl]paclitaxel methanesulfonate (Compound No. C18): ESI-MS m/z [M+H]+ 999.42

2'-O-[4-N,N-diethylamino-2(S)-fluorobutyryl]paclitaxel fumarate (Compound No. C19): ESI-MS m/z [M+H]+ 1013.41

2'-O-[4-N-methyl-N-isopropylamino-2(R,S)-fluorobutyryl]paclitaxel hydrochloride (Compound No. C20): ESI-MS m/z [M+H]+ 1013.43

2'-O-[4-N,N-dimethylamino-2(R,S)-2-trifluoromethylbutyryl]paclitaxel p-toluene sulfonate (Compound No. C21): ESI-MS m/z [M+H]+ 1035.38

2'-O-[4-N,N-dimethylamino-2(R,S)-2-difluoromethylbutyryl]paclitaxel hydrochloride (Compound No. C22): ESI-MS m/z [M+H]+ 1017.23

2'-O-[4-N,N-dimethylamino-2(R)-fluorovaleryl]paclitaxel maleate (Compound No. C23): ESI-MS m/z [M+H]+ 999.34

2'-O-[4-N,N-dimethylamino-2(S)-2-difluoromethylhexanoyl]paclitaxel sulfate (Compound No. C24): ESI-MS m/z [M+H]+ 1045.44

2'-O-[4-N-methyl-N-ethylamino-2(R)-fluorobutyryl]docetaxel methanesulfonate (Compound No. C25): ESI-MS m/z [M+H]+ 953.44

2'-O-[4-N,N-diethylamino-2(S)-fluorobutyryl]docetaxel maleate (Compound No. C26): ESI-MS m/z [M+H]+ 967.45

2'-O-[4-N-methyl-N-isopropylamino-2(R)-fluorobutyryl]docetaxel hydrochloride (Compound No. C27): ESI-MS m/z [M+H]+ 967.42

2'-O-[4-N,N-dimethylamino-2(R)-2-trifluoromethylbutyryl]docetaxel methanesulfonate (Compound No. C28): ESI-MS m/z [M+H]+ 989.38

2'-O-[4-N,N-dimethylamino-2(R,S)-2-difluoromethylbutyryl]docetaxel hydrochloride (Compound No. C29): ESI-MS m/z [M+H]+ 971.35

2'-O-[4-N,N-dimethylamino-2(R,S)-fluorovaleryl]docetaxel methanesulfonate (Compound No. C30): ESI-MS m/z [M+H]+ 953.47

2'-O-[4-N,N-dimethylamino-2(S)-fluorohexanoyl]docetaxel sulfate (Compound No. C31): ESI-MS m/z [M+H]+ 967.41

2'-O-[4-N-methyl-N-ethylamino-2(R)-fluorobutyryl]cabazitaxel maleate (Compound No. C32): ESI-MS m/z [M+H]+ 981.35

2'-O-[4-N,N-diethylamino-2(R)-fluorobutyryl]cabazitaxel methanesulfonate (Compound No. C33): ESI-MS m/z [M+H]+ 995.51

2'-O-[4-N-methyl-N-isopropylamino-2(R)-fluorobutyryl]cabazitaxel hydrochloride (Compound No. C34): ESI-MS m/z [M+H]+ 995.47

2'-O-[4-N,N-dimethylamino-2(R)-2-trifluoromethylbutyryl]cabazitaxel methanesulfonate (Compound No. C35): ESI-MS m/z [M+H]+ 1017.52

2'-O-[4-N,N-dimethylamino-2(R)-2-difluoromethylbutyryl]cabazitaxel p-toluene sulfonate (Compound No. C36): ESI-MS m/z [M+H]+ 999.46

2'-O-[4-N,N-dimethylamino-2(R)-fluorovaleryl]cabazitaxel hydrochloride (Compound No. C37): ESI-MS m/z [M+H]+ 981.33

2'-O-[4-N,N-dimethylamino-2(R)-fluorohexanoyl]cabazitaxel sulfate (Compound No. C38): ESI-MS m/z [M+H]+ 995.34

2'-O-[4-N-methyl-N-ethylamino-2(R,S)-fluorobutyryl]larotaxel hydrochloride (Compound No. C40): ESI-MS m/z [M+H]+ 977.54

2'-O-[4-N-methyl-N-isopropylamino-2(R,S)-2-trifluoromethylbutyryl]larotaxel maleate (Compound No. C41): ESI-MS m/z [M+H]+ 1041.35

2'-O-[4-N,N-dimethylamino-2(S)-fluorovaleryl]larotaxel phosphate (Compound No. C42): ESI-MS m/z [M+H]+ 977.65

2'-O-[4-N,N-diethylamino-2(S)-fluorobutyryl]tesetaxel hydrochloride (Compound No. C44): ESI-MS m/z [M+H]+ 1041.52

2'-O-[4-N-methyl-N-isopropylamino-2(R,S)-2-trifluoromethylbutyryl]tesetaxel succinate (Compound No. C45): ESI-MS m/z [M+H]+ 1091.51

2'-O-[4-(pyrrolidin-1-yl)amino-2(R,S)-fluorovaleryl]tesetaxel sulfate (Compound No. C46): ESI-MS m/z [M+H]+ 1053.48

2'-O-[4-N,N-diethylamino-2(R)-fluorobutyryl]paclitaxel hydrochloride (Compound No. C51): ESI-MS m/z [M+H]+ 1013.35

2'-O-[3-N,N-dimethylamino-2(R,S)-fluoropropionyl]paclitaxel hydrochloride (Compound No. C52): ESI-MS m/z [M+H]+ 971.28

2'-O-[4-N-benzylamino-2(S)-fluorobutyryl]docetaxel hydrochloride (Compound No. C62): ESI-MS m/z [M+H]+ 1001.36

2'-O-[3-(N,N-diethyl)amino-2(R,S)-trifluoromethylpropionyl]docetaxel hydrochloride (Compound No. C63): ESI-MS m/z [M+H]+ 1003.34

2'-O-[4-(N-methyl)amino-2(R)-trifluoromethylbutyryl]paclitaxel hydrochloride (Compound No. C65): ESI-MS m/z [M+H]+ 1021.24

2'-O-[3-(N-isopropyl)amino-2(R,S)-difluoromethylpropionyl]cabazitaxel hydrochloride (Compound No. C66): ESI-MS m/z [M+H]+ 999.38

2'-O-[5-(N,N-dimethyl)amino-2(R)-fluorovaleryl]paclitaxel hydrochloride (Compound No. C74): ESI-MS m/z [M+H]+ 999.33

2'-O-[4-(N,N-dimethyl)amino-2(S)-trifluoromethylbutyryl]cabazitaxel hydrochloride (Compound No. C75): ESI-MS m/z [M+H]+ 1017.41

2'-O-[4-(N-isopropyl)amino-2(R,S)-trifluoromethylbutyryl]paclitaxel hydrochloride (Compound No. C76): ESI-MS m/z [M+H]+ 1049.37

2'-O-[5-N,N-dimethylamino-2(S)-trifluoromethylvaleryl]docetaxel hydrochloride (Compound No. C79): ESI-MS m/z [M+H]+ 1003.31

2'-O-[4-N-benzylamino-2-methyl-2(R,S)-fluorobutyryl]paclitaxel hydrochloride (Compound No. C80): ESI-MS m/z [M+H]+ 1061.32

2'-O-[4-N,N-dimethylamino-2(R)-difluoromethylbutyryl]docetaxel hydrochloride (Compound No. C87): ESI-MS m/z [M+H]+ 971.29

2'-O-[3-cyclopentylamino-2-ethyl-2(R,S)-trifluoromethylpropionyl]docetaxel hydrochloride (Compound No. C95): ESI-MS m/z [M+H]+ 1001.31

2'-O-[5-N-benzylamino-2-benzyl-2(R)-difluoromethylvaleryl]cabazitaxel hydrochloride (Compound No. C97): ESI-MS m/z [M+H]+ 1075.42

2'-O-[4-(4-piperidin-1-yl)-2(S)-trifluoromethylbutyryl]cabazitaxel hydrochloride (Compound No. C99): ESI-MS m/z [M+H]+ 1057.35

2'-O-[4-N,N-dimethylamino-2(S)-fluorobutyryl]larotaxel hydrochloride (Compound No. C102): ESI-MS m/z [M+H]+ 963.34

2'-O-[4-N,N-dimethylamino-2(R)-fluorobutyryl]tesetaxel hydrochloride (Compound No. C107): ESI-MS m/z [M+H]+ 1013.41.

The inventors provide the following experimental examples to show the surprising and unexpected beneficial effects of the water soluble taxane derivatives of the present invention.

EXPERIMENTAL EXAMPLES

Experimental Example 1.1. Solubility in Physiological Saline

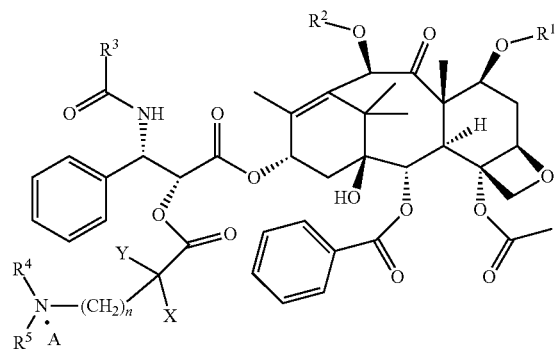

(Ia-1)

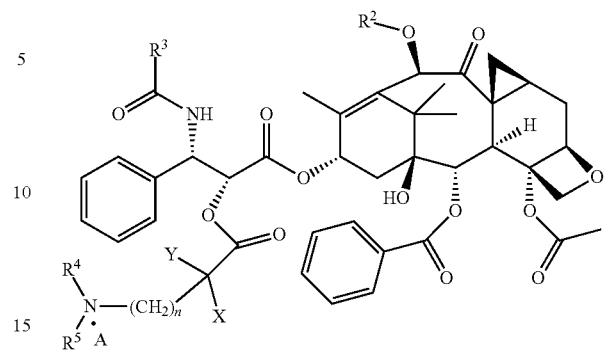

(Ia-2)

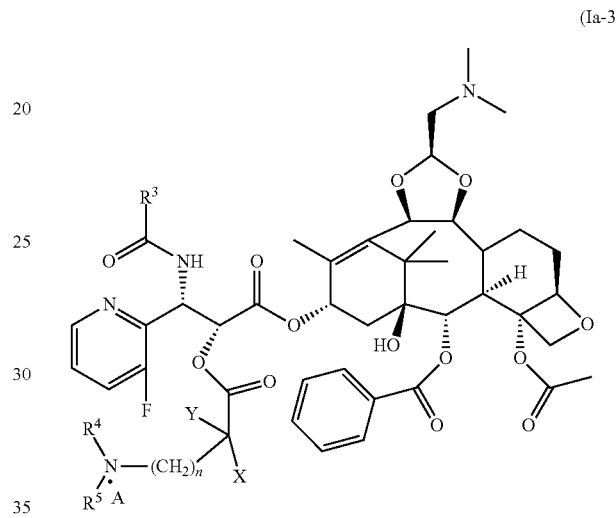

(Ia-3)

TABLE 1

Solubility of the water soluble taxane derivatives in physiological saline

| Compd. No. | Type of the parent ring | n | $R^1$ | $R^2$ | $R^3$ | $R^4$ | $R^5$ | X | Y | C* | A | Solubility (mg/ml) |
|---|---|---|---|---|---|---|---|---|---|---|---|---|
| 01 | I-1 | 2 | H | Ac | Ph | Me | Me | H | F | R | HCl | 1.1 |
| 02 | I-1 | 2 | H | Ac | Ph | Me | Me | H | F | S | HCl | 1.2 |
| 03 | I-1 | 2 | H | Ac | Ph | Me | Me | H | F | R, S | HCl | 1.1 |
| 04 | I-1 | 2 | H | H | t-BuO | Me | Me | H | F | R | HCl | 2.8 |
| 05 | I-1 | 2 | H | H | t-BuO | Me | Me | H | F | S | HCl | 2.5 |
| 06 | I-1 | 2 | H | H | t-BuO | Me | Me | H | F | R, S | HCl | 2.6 |
| 07 | I-1 | 2 | Me | Me | t-BuO | Me | Me | H | F | R | HCl | 1.5 |
| 08 | I-1 | 2 | Me | Me | t-BuO | Me | Me | H | F | S | HCl | 1.3 |
| 09 | I-1 | 2 | Me | Me | t-BuO | Me | Me | H | F | R, S | HCl | 1.3 |
| 10 | I-1 | 2 | Me | Me | t-BuO | H | H | H | $CHF_2$ | R | $NaHSO_4$ | 1.6 |
| 11 | I-1 | 2 | Me | Me | t-BuO | Et | Et | $CH_3$ | $CF_3$ | R | $MeSO_3H$ | 11.2 |
| 12 | I-1 | 3 | H | H | t-BuO | Me | Et | H | $CF_2CH_3$ | R | HCl | 1.2 |
| 13 | I-1 | 3 | H | H | t-BuO | Me | Me | H | F | R | $MeSO_3H$ | 15.6 |
| 16 | I-2 | 3 | | Ac | t-BuO | Me | Me | H | F | R | $MeSO_3H$ | 11.1 |
| 17 | I-3 | 3 | | | t-BuO | Me | Me | H | F | R | $MeSO_3H$ | 12.3 |
| C1 | I-1 | 2 | H | Ac | Ph | Me | Me | H | F | R | $MeSO_3H$ | 10.5 |
| C2 | I-1 | 2 | H | Ac | Ph | Me | Me | H | F | S | $MeSO_3H$ | 10.4 |
| C3 | I-1 | 2 | H | Ac | Ph | Me | Me | H | F | R, S | $MeSO_3H$ | 10.3 |
| C4 | I-1 | 2 | H | H | t-BuO | Me | Me | H | F | R | $MeSO_3H$ | 12.4 |
| C5 | I-1 | 2 | H | H | t-BuO | Me | Me | H | F | S | $MeSO_3H$ | 12.7 |
| C6 | I-1 | 2 | H | H | t-BuO | Me | Me | H | F | R, S | $MeSO_3H$ | 12.5 |
| C7 | I-1 | 2 | Me | Me | t-BuO | Me | Me | H | F | R | $MeSO_3H$ | 0.9 |
| C8 | I-1 | 2 | Me | Me | t-BuO | Me | Me | H | F | S | $MeSO_3H$ | 0.6 |
| C9 | I-1 | 2 | Me | Me | t-BuO | Me | Me | H | F | R, S | $MeSO_3H$ | 0.4 |
| C10 | I-1 | 2 | Me | Me | t-BuO | H | H | H | $CHF_2$ | R | $H_2SO_4$ | 0.8 |
| C11 | I-1 | 2 | Me | Me | t-BuO | Et | Et | $CH_3$ | $CF_3$ | R | HCl | 1.1 |
| C12 | I-1 | 3 | H | H | t-BuO | Me | Et | H | $CF_2CH_3$ | R | $MeSO_3H$ | 11.3 |
| C13 | I-1 | 3 | H | H | t-BuO | Me | Me | H | F | R | HCl | 2.3 |

TABLE 1-continued

Solubility of the water soluble taxane derivatives in physiological saline

| Compd. No. | Type of the parent ring | n | $R^1$ | $R^2$ | $R^3$ | $R^4$ | $R^5$ | X | Y | C* | A | Solubility (mg/ml) |
|---|---|---|---|---|---|---|---|---|---|---|---|---|
| C16 | I-2 | 3 | | Ac | t-BuO | Me | Me | H | F | R | HCl | 0.8 |
| C17 | I-3 | 3 | | | t-BuO | Me | Me | H | F | R | HCl | 1.0 |

Experimental Example 2. In Vitro Dissociation in Blood Plasma of Rat

The obtained water soluble taxane derivatives of the following formulae were formulated as 0.2 mg/ml aqueous solutions. 0.1 ml samples were taken from each of the solutions, added respectively to 0.9 ml of fresh blood plasma (anticoagulated with heparin) from SD rats, homogeneously mixed, and placed in a thermostatic water bath at 37° C. for incubation with time being recorded. After 2 min, 5 min and 10 min of incubation, 0.2 ml of solutions were respectively taken from each of the samples, and added to acetonitrile (0.4 ml) cooled to −20° C. for precipitation of protein. The samples were shaken and centrifuged for 10 min (10,000 rpm), and the supernatant was then taken for HPLC analysis. The results are presented in following Table 2:

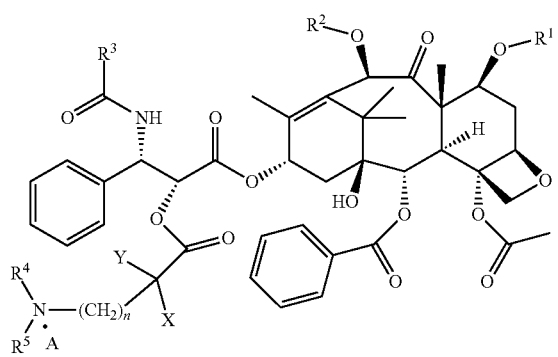
(Ia-1)

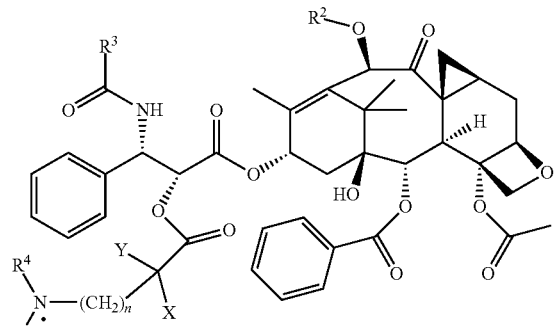
(Ia-2)

-continued

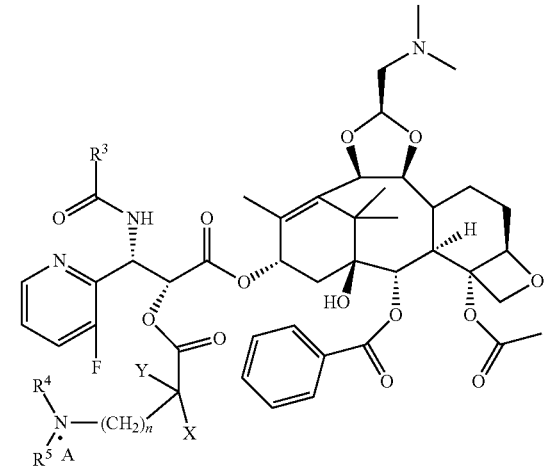
(Ia-3)

TABLE 2

Test of in vitro dissociation of the water soluble taxane derivatives in blood plasma of rat

| Compd. No. | Type of the parent ring | n | $R^1$ | $R^2$ | $R^3$ | $R^4$ | $R^5$ | X | Y | C* | A | 2 min | 5 min | 10 min |
|---|---|---|---|---|---|---|---|---|---|---|---|---|---|---|
| 01 | I-1 | 2 | H | Ac | Ph | Me | Me | H | F | R | HCl | 63.5 | 96.8 | 100 |
| 02 | I-1 | 2 | H | Ac | Ph | Me | Me | H | F | S | HCl | 59.8 | 95.6 | 100 |
| 03 | I-1 | 2 | H | Ac | Ph | Me | Me | H | F | R, S | HCl | 61.8 | 93.1 | 100 |
| 04 | I-1 | 2 | H | H | t-BuO | Me | Me | H | F | R | HCl | 58.6 | 92.6 | 100 |
| 05 | I-1 | 2 | H | H | t-BuO | Me | Me | H | F | S | HCl | 56.4 | 91.1 | 100 |
| 06 | I-1 | 2 | H | H | t-BuO | Me | Me | H | F | R, S | HCl | 56.4 | 91.1 | 100 |
| 07 | I-1 | 2 | Me | Me | t-BuO | Me | Me | H | F | R | HCl | 49.5 | 89.6 | 100 |
| 08 | I-1 | 2 | Me | Me | t-BuO | Me | Me | H | F | S | HCl | 47.6 | 87.6 | 100 |
| 09 | I-1 | 2 | Me | Me | t-BuO | Me | Me | H | F | R, S | HCl | 47.8 | 89.1 | 100 |
| 10 | I-1 | 2 | Me | Me | t-BuO | H | H | H | $CHF_2$ | R | $NaHSO_4$ | 45.2 | 86.5 | 96.8 |
| 11 | I-1 | 2 | Me | Me | t-BuO | Et | Et | $CH_3$ | $CF_3$ | R | $MeSO_3H$ | 52.3 | 89.6 | 97.2 |
| 12 | I-1 | 3 | H | H | t-BuO | Me | Et | H | $CF_2CH_3$ | R | HCl | 43.6 | 75.6 | 89.6 |
| 13 | I-1 | 3 | H | H | t-BuO | Me | Me | H | F | R | $MeSO_3H$ | 45.7 | 85.2 | 92.3 |
| 14 | I-1 | 5 | H | H | t-BuO | —$(CH_2)_2$— | | F | F | — | $MeSO_3H$ | 42.1 | 55.7 | 72.5 |

TABLE 2-continued

Test of in vitro dissociation of the water soluble taxane derivatives in blood plasma of rat

| Compd. No. | Type of the parent ring | n | $R^1$ | $R^2$ | $R^3$ | $R^4$ | $R^5$ | X | Y | C* | A | 2 min | 5 min | 10 min |
|---|---|---|---|---|---|---|---|---|---|---|---|---|---|---|
| 15 | I-1 | 6 | H | Ac | Ph | Me | cyclopentyl-Me | F | $CF_3$ | R, S | $MeSO_3H$ | 35.0 | 46.2 | 57.9 |
| 16 | I-2 | 3 |  | Ac | t-BuO | Me | Me | H | F | R | $MeSO_3H$ | 60.2 | 92.1 | 100 |
| 17 | I-3 | 3 |  |  | t-BuO | Me | Me | H | F | R | $MeSO_3H$ | 59.3 | 93.5 | 100 |
| C1 | I-1 | 2 | H | Ac | Ph | Me | Me | H | F | R | $MeSO_3H$ | 64.3 | 97.0 | 100 |
| C2 | I-1 | 2 | H | Ac | Ph | Me | Me | H | F | S | $MeSO_3H$ | 62.8 | 96.5 | 100 |
| C3 | I-1 | 2 | H | Ac | Ph | Me | Me | H | F | R, S | $MeSO_3H$ | 63.7 | 96.8 | 100 |
| C4 | I-1 | 2 | H | H | t-BuO | Me | Me | H | F | R | $MeSO_3H$ | 59.2 | 93.4 | 100 |
| C5 | I-1 | 2 | H | H | t-BuO | Me | Me | H | F | S | $MeSO_3H$ | 58.9 | 93.3 | 100 |
| C6 | I-1 | 2 | H | H | t-BuO | Me | Me | H | F | R, S | $MeSO_3H$ | 59.1 | 93.3 | 100 |
| C7 | I-1 | 2 | Me | Me | t-BuO | Me | Me | H | F | R | $MeSO_3H$ | 49.7 | 88.9 | 100 |
| C8 | I-1 | 2 | Me | Me | t-BuO | Me | Me | H | F | S | $MeSO_3H$ | 49.4 | 88.4 | 100 |
| C9 | I-1 | 2 | Me | Me | t-BuO | Me | Me | H | F | R, S | $MeSO_3H$ | 49.3 | 88.6 | 100 |
| C10 | I-1 | 2 | Me | Me | t-BuO | H | H | H | $CHF_2$ | R | $H_2SO_4$ | 45.6 | 87.1 | 97.3 |
| C11 | I-1 | 2 | Me | Me | t-BuO | Et | Et | $CH_3$ | $CF_3$ | R | HCl | 51.2 | 88.4 | 95.9 |
| C12 | I-1 | 3 | H | H | t-BuO | Me | Et | H | $CF_2CH_3$ | R | $MeSO_3H$ | 42.8 | 74.8 | 88.4 |
| C13 | I-1 | 3 | H | H | t-BuO | Me | Me | H | F | R | HCl | 44.8 | 84.8 | 92.7 |
| C14 | I-1 | 5 | H | H | t-BuO |  | —$(CH_2)_2$— | F | F | — | HCl | 41.9 | 54.4 | 71.3 |
| C15 | I-1 | 6 | H | Ac | Ph | Me | cyclopentyl-Me | F | $CF_3$ | R, S | HCl | 34.2 | 45.3 | 58.2 |
| C16 | I-2 | 3 |  | Ac | t-BuO | Me | Me | H | F | R | HCl | 61.1 | 93.8 | 100 |
| C17 | I-3 | 3 |  |  | t-BuO | Me | Me | H | F | R | HCl | 60.7 | 95.5 | 100 |

Experimental Example 3. In Vitro Dissociation in Blood Plasma of Rabbit

The obtained water soluble taxane derivatives of the following formulae were formulated as 0.2 mg/ml aqueous solutions. 0.1 ml samples were taken from each of the solutions, added respectively to 0.9 ml of fresh blood plasma (anticoagulated with heparin) from New Zealand white rabbits, homogeneously mixed, and placed m a thermostatic water bath at 37° C. for incubation with time being recorded. After 5 min, 20 min and 60 min of incubation, 0.2 ml of solutions were respectively taken from each of the samples, and added to acetonitrile (0.4 ml) cooled to −20° C. for precipitation of protein. The samples were shaken and centrifuged for 10 min (10.000 rpm), and the supernatant was then taken for HPLC analysis. The results are presented in following Table 3:

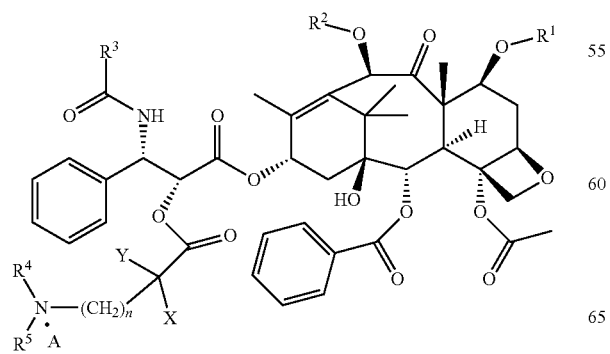

(Ia-1)

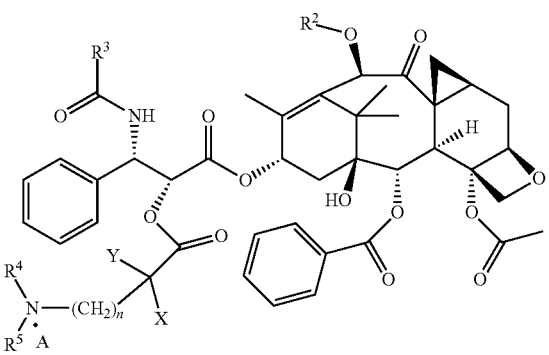

(Ia-2)

-continued

-continued

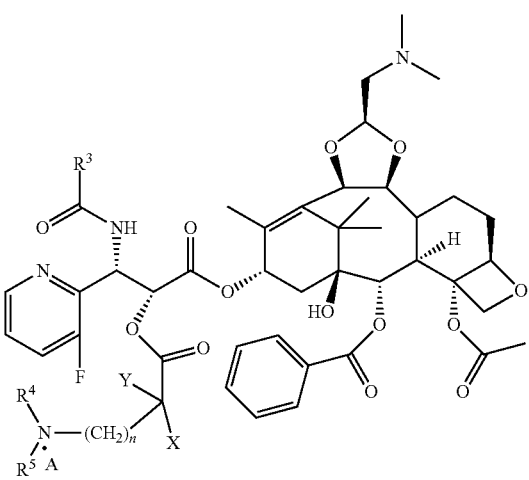

(Ia-3)

tration, 0.3 ml of venous blood was taken from the retrobulbar venous plexus of the rats, placed in heparinized tubes, and centrifuged at 11.000 rpm for 5 min. Blood plasma was separated, and the concentrations of the compounds in the blood plasma were determined by liquid chromatography-mass spectrometry.

4.2. Results:

After intravenous injection of compounds 01, 02, and 03, compounds 01, 02, and 03 cannot be detected in the blood plasma, and only paclitaxel can be detected.

The mean concentrations (ng/ml) of paclitaxel in the blood plasma of animals from each group were 1789, 1637, 1825, and 1793, respectively.

Experimental Example 5. In Vivo Metabolic Test of the Water Soluble Docetaxel Derivatives in Rats 5.1. Method of Study:

12 SD rats (male, body weight: 200-220) g) were randomly divided into four groups, and intravenously administered with 5 mg/kg of compounds 04, 05, 06 and com-

TABLE 3

Test of in vitro dissociation of the water soluble taxane derivatives in blood plasma of rabbit

| Compd. No. | Type of the parent ring | n | $R^1$ | $R^2$ | $R^3$ | $R^4$ | $R^5$ | X | Y | C* | A | Sampling time/dissociation percent (%) | | |
|---|---|---|---|---|---|---|---|---|---|---|---|---|---|---|
| | | | | | | | | | | | | 2 min | 5 min | 10 min |
| 01 | I-1 | 2 | H | Ac | Ph | Me | Me | H | F | R | HCl | 76.5 | 98.3 | 100 |
| 02 | I-1 | 2 | H | Ac | Ph | Me | Me | H | F | S | HCl | 68.2 | 97.5 | 100 |
| 03 | I-1 | 2 | H | Ac | Ph | Me | Me | H | F | R, S | HCl | 75.7 | 93.5 | 100 |
| 04 | I-1 | 2 | H | H | t-BuO | Me | Me | H | F | R | HCl | 80.2 | 93.5 | 100 |
| 05 | I-1 | 2 | H | H | t-BuO | Me | Me | H | F | S | HCl | 79.3 | 91.8 | 100 |
| 06 | I-1 | 2 | H | H | t-BuO | Me | Me | H | F | R, S | HCl | 75.6 | 98.6 | 100 |
| 07 | I-1 | 2 | Me | Me | t-BuO | Me | Me | H | F | R | HCl | 79.2 | 95.5 | 100 |
| 08 | I-1 | 2 | Me | Me | t-BuO | Me | Me | H | F | S | HCl | 89.9 | 93.2 | 100 |
| 09 | I-1 | 2 | Me | Me | t-BuO | Me | Me | H | F | R, S | HCl | 83.2 | 97.1 | 100 |
| 10 | I-1 | 2 | Me | Me | t-BuO | H | H | H | $CHF_2$ | R | $NaHSO_4$ | 38.1 | 63.2 | 80.3 |
| 11 | I-1 | 2 | Me | Me | t-BuO | Et | Et | $CH_3$ | $CF_3$ | R | $MeSO_3H$ | 56.2 | 80.5 | 92.1 |
| 12 | I-1 | 3 | H | H | t-BuO | Me | Et | H | $CF_2CH_3$ | R | HCl | 35.2 | 61.3 | 73.2 |
| 13 | I-1 | 3 | H | H | t-BuO | Me | Me | H | F | R | $MeSO_3H$ | 33.2 | 55.8 | 62.1 |
| 16 | I-2 | 3 | | Ac | t-BuO | Me | Me | H | F | R | $MeSO_3H$ | 63.2 | 94.1 | 100 |
| 17 | I-3 | 3 | | | t-BuO | Me | Me | H | F | R | $MeSO_3H$ | 62.7 | 93.4 | 100 |
| C1 | I-1 | 2 | H | Ac | Ph | Me | Me | H | F | R | $MeSO_3H$ | 77.2 | 98.4 | 100 |
| C2 | I-1 | 2 | H | Ac | Ph | Me | Me | H | F | S | $MeSO_3H$ | 69.7 | 98.1 | 100 |
| C3 | I-1 | 2 | H | Ac | Ph | Me | Me | H | F | R, S | $MeSO_3H$ | 76.5 | 94.6 | 100 |
| C4 | I-1 | 2 | H | H | t-BuO | Me | Me | H | F | R | $MeSO_3H$ | 81.6 | 94.8 | 100 |
| C5 | I-1 | 2 | H | H | t-BuO | Me | Me | H | F | S | $MeSO_3H$ | 81.2 | 93.1 | 100 |
| C6 | I-1 | 2 | H | H | t-BuO | Me | Me | H | F | R, S | $MeSO_3H$ | 76.8 | 97.8 | 100 |
| C7 | I-1 | 2 | Me | Me | t-BuO | Me | Me | H | F | R | $MeSO_3H$ | 78.4 | 94.8 | 100 |
| C8 | I-1 | 2 | Me | Me | t-BuO | Me | Me | H | F | S | $MeSO_3H$ | 85.6 | 94.5 | 100 |
| C9 | I-1 | 2 | Me | Me | t-BuO | Me | Me | H | F | R, S | $MeSO_3H$ | 81.2 | 96.7 | 100 |
| C10 | I-1 | 2 | Me | Me | t-BuO | H | H | H | $CHF_2$ | R | $H_2SO_4$ | 48.9 | 68.4 | 91.3 |
| C11 | I-1 | 2 | Me | Me | t-BuO | Et | Et | $CH_3$ | $CF_3$ | R | HCl | 61.2 | 84.5 | 96.3 |
| C12 | I-1 | 3 | H | H | t-BuO | Me | Et | H | $CF_2CH_3$ | R | $MeSO_3H$ | 44.6 | 72.1 | 89.6 |
| C13 | I-1 | 3 | H | H | t-BuO | Me | Me | H | F | R | HCl | 46.2 | 78.9 | 93.4 |
| C16 | I-2 | 3 | | Ac | t-BuO | Me | Me | H | F | R | HCl | 68.2 | 94.4 | 100 |
| C17 | I-3 | 3 | | | t-BuO | Me | Me | H | F | R | HCl | 69.7 | 96.8 | 100 |

Experimental Example 4. In Vivo Metabolic Test of the Water Soluble Paclitaxel Derivatives in Rats 4.1. Method of Study:

12 SD rats (male, body weight: 200-220 g) were randomly divided into four groups, and intravenously administered with 5 mg/kg of compounds 01, 02, 03 and commercially available paclitaxel in a volume of 5 ml/kg, respectively. Compounds 01, 02 and 03 were formulated with 5% dextrose injection (pH=5), and paclitaxel is in the form of a commercially available injection. After 5 min of adminismercially available docetaxel m a volume of 5 ml/kg, respectively. Compounds 04, 05 and 06 were formulated with 5% dextrose injection (pH=5), and docetaxel is in the form of a commercially available injection. After 5 min of administration, 0.3 ml of venous blood was taken from the retrobulbar venous plexus of the rats, placed in heparinized tubes, and centrifuged at 11,000 rpm for 5 min. Plasma was separated, and the concentrations of the compounds in the plasma were determined by liquid chromatography □-mass spectrometry.

5.2. Results:

After intravenous injection of compounds 04, 05, and 06, compounds 04, 05, and 06 cannot be detected in the blood plasma, and only docetaxel can be detected.

The mean concentrations (ng/ml) of docetaxel in the blood plasma of animals from each group were 1506, 1387, 1621, and 769, respectively.

Experimental Example 6. Antitumor Activity Test of the Water Soluble Taxane Derivatives 6.1. Test of the Inhibitory Activity of the Water Soluble Paclitaxel Derivatives on Subcutaneously Xenografted Tumor of Human Ovarian Cancer SK-OV-3 in Nude Mice Purpose: to evaluate and compare the inhibitory activity of the water soluble paclitaxel derivatives, paclitaxel and Abraxane® on subcutaneously xenografted tumor of human ovarian cancer SK-OV-3 in nude mice.

Dosage Regimen and Experimental Procedures:

Human ovarian cancer SK-OV-3 cells were subcutaneously inoculated to nude mice. After the tumor volume reached 100-150 mm³, the animals were randomly divided into groups (D0), and administered with the water soluble paclitaxel derivatives of the following formula, paclitaxel, and Abraxane®, respectively once per day for 5 days. The dosage and dosage regimen are shown in following table 4. The tumor volume was measured 2-3 times per week, the animals were weighed and the data were recorded until day 22 (D22) after grouping.

The tumor volume (V) was calculated according to the equation: $V = \frac{1}{2} \times a \times b^2$, wherein a and b represent the length and the width, respectively.

$T/C\ (\%) = (T - T_0)/(C - C_0) \times 100$, wherein T and C represent the tumor volume at the end of the experiment, and $T_0$ and $C_0$ represent the tumor volume at the beginning of the experiment.

The antitumor activity data are shown in following Table 4:

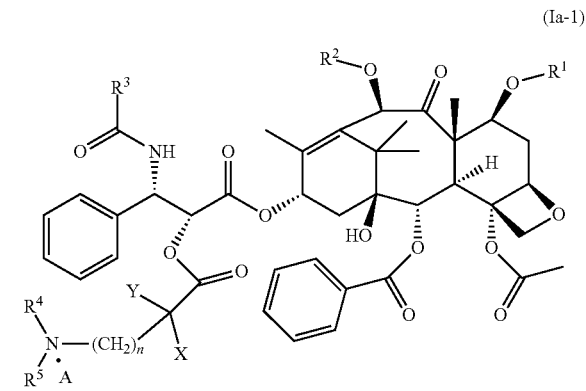

(Ia-1)

TABLE 4

The inhibitory activity of the water soluble paclitaxel derivatives, paclitaxel and Abraxane ® on subcutaneously xenografted tumor of human ovarian cancer SK-OV-3 in nude mice

| Compd. No. | Dosage | Time and route of administration | n | R¹ | R² | R³ | R⁴ | R⁵ | X | Y | C* | A |
|---|---|---|---|---|---|---|---|---|---|---|---|---|
| the control group | — | D0-4 IV | — | — | — | — | — | — | — | — | — | — |
| paclitaxel | 16 mg/kg | D0-4 IV | — | — | — | — | — | — | — | — | — | — |
| Abraxane ® | 24 mg/kg | D0-4 IV | — | — | — | — | — | — | — | — | — | — |
| C1 | 24 mg/kg | D0-4 IV | 2 | H | Ac | Ph | Me | Me | H | F | R | MeSO₃H |
| C2 | 24 mg/kg | D0-4 IV | 2 | H | Ac | Ph | Me | Me | H | F | S | MeSO₃H |
| C3 | 24 mg/kg | D0-4 IV | 2 | H | Ac | Ph | Me | Me | H | F | R, S | MeSO₃H |
| C18 | 24 mg/kg | D0-4 IV | 2 | H | Ac | Ph | Et | Me | H | F | R | MeSO₃H |
| C19 | 24 mg/kg | D0-4 IV | 2 | H | Ac | Ph | Et | Et | H | F | S | fumaric acid |
| C20 | 24 mg/kg | D0-4 IV | 2 | H | Ac | Ph | Me | i-Pro | H | F | R, S | HCl |
| C21 | 24 mg/kg | D0-4 IV | 2 | H | Ac | Ph | Me | Me | H | CF₃ | R, S | p-toluene sulfonic acid |
| C22 | 24 mg/kg | D0-4 IV | 2 | H | Ac | Ph | Me | Me | H | CHF₂ | R, S | HCl |
| C23 | 24 mg/kg | D0-4 IV | 3 | H | Ac | Ph | Me | Me | H | F | R | maleic acid |
| C24 | 24 mg/kg | D0-4 IV | 4 | H | Ac | Ph | Me | Me | H | CHF₂ | S | sulfuric acid |

| | Anti-tumor activity data | | | | |
|---|---|---|---|---|---|
| Compd. No. | Tumor volume (mm³) (D0) | Tumor volume (mm³) (D22) | T/C (%) D22 | Tumor inhibitory percent (%)^Δ D22 | Body weight change (%) D4 |
| the control group | 134.6 ± 18.3 | 980.4 ± 271.9 | — | — | −11 |
| paclitaxel | 134.6 ± 19.7 | 53.7 ± 11.2 | −60 | 160 | −4.8 |
| Abraxane ® | 126.0 ± 10.7 | 53.8 ± 13.9 | −57 | 157 | −8.2 |
| C1 | 133.6 ± 9.5 | 49.8 ± 10.4 | −63 | 163 | −5.9 |
| C2 | 134.3 ± 10.4 | 51.2 ± 11.2 | −61 | 158 | −5.8 |
| C3 | 133.4 ± 10.4 | 50.6 ± 9.7 | −64 | 165 | −6.0 |
| C18 | 133.6 ± 9.4 | 55.7 ± 10.6 | −53 | 137 | −7.0 |
| C19 | 133.6 ± 9.4 | 55.7 ± 10.1 | −44 | 114 | −8.1 |
| C20 | 127.9 ± 11.4 | 60.4 ± 12.3 | −38 | 98 | −10.3 |

TABLE 4-continued

The inhibitory activity of the water soluble paclitaxel derivatives, paclitaxel and Abraxane ® on subcutaneously xenografted tumor of human ovarian cancer SK-OV-3 in nude mice

| | | | | | |
|---|---|---|---|---|---|
| C21 | 134.9 ± 11.4 | 57.3 ± 11.4 | −48 | 124 | −8.9 |
| C22 | 133.4 ± 12.6 | 61.2 ± 13.5 | −35 | 135 | −8.4 |
| C23 | 135.8 ± 14.7 | 70.8 ± 16.8 | −23 | 60 | −9.4 |
| C24 | 133.8 ± 12.2 | 79.8 ± 12.8 | −14 | 36 | −11.6 |

D0: the time of administration for the first time;
$^\Delta P_{(D22)}$ = 0.000, compared to the control, using Student's t-test.
The numbers of mice at the beginning of the experiment: n = 10 in the control group, and n = 6 in the administered group.
C* is the configuration of the chiral carbon in the side chain of an amino acid.
Conclusion: the water soluble paclitaxel derivatives have an inhibitory effect on human ovarian cancer SK-OV-3.

6.2. Test of the Inhibitory Activity of the Water Soluble Docetaxel Derivatives on Subcutaneously Xenografted Tumor of Human Prostate Cancer PC-3 in Nude Mice Purpose: to evaluate and compare the inhibitory activity of the water soluble docetaxel derivatives and docetaxel on subcutaneously xenografted tumor of human prostate cancer PC-3 in nude mice Dosage Regimen and Experimental Procedures:

Human prostate cancer PC-3 cells were subcutaneously inoculated into nude mice. After the tumor volume reached 100-150 mm$^3$, the animals were randomly divided into several groups, and administered with the water soluble docetaxel derivatives of the following formula and docetaxel, respectively once on the same day (D0). The dosage and dosage regimen are shown in following table 5. The tumor volume was measured 2-3 times per week, the animals were weighed and the data were recorded until day 20 (D20) after grouping.

The tumor volume (V) was calculated according to the equation: V=½×a×b$^2$, wherein a and b represent the length and the width, respectively.

T/C (%)=(T−T$_0$)/(C−C$_0$)×100, wherein T and C represent the tumor volume at the end of the experiment; and T$_0$ and C$_0$ represent the tumor volume at the beginning of the experiment.

The antitumor activity data are shown in following Table 5:

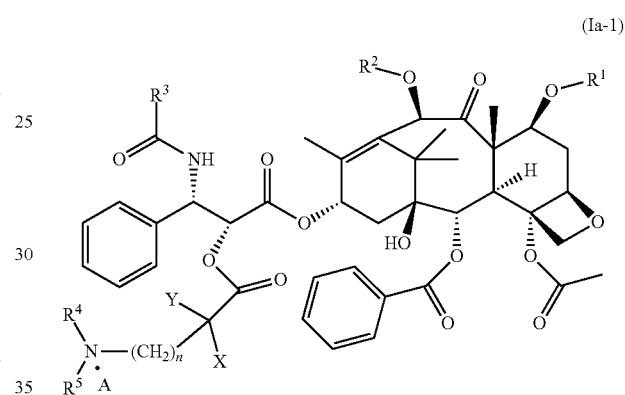

(Ia-1)

TABLE 5

The inhibitory activity of the water soluble docetaxel derivatives and docetaxel on subcutaneously xenografted tumor of human prostate cancer PC-3 in nude mice.

| Compd. No. | Dosage | Time and route of administration | n | R$^1$ | R$^2$ | R$^3$ | R$^4$ | R$^5$ | X | Y | C* | A |
|---|---|---|---|---|---|---|---|---|---|---|---|---|
| the control group | — | D0 IV | — | — | — | — | — | — | — | — | — | — |
| docetaxel | 14 mg/kg | D0 IV | — | — | — | — | — | — | — | — | — | — |
| C4 | 33.6 mg/kg | D0 IV | 2 | H | H | t-BuO | Me | Me | H | F | R | MeSO$_3$H |
| C5 | 33.6 mg/kg | D0 IV | 2 | H | H | t-BuO | Me | Me | H | F | S | MeSO$_3$H |
| C6 | 33.6 mg/kg | D0 IV | 2 | H | H | t-BuO | Me | Me | H | F | R, S | MeSO$_3$H |
| C25 | 33.6 mg/kg | D0 IV | 2 | H | H | t-BuO | Et | Me | H | F | R | MeSO$_3$H |
| C26 | 33.6 mg/kg | D0 IV | 2 | H | H | t-BuO | Et | Et | H | F | S | maleic acid |
| C27 | 33.6 mg/kg | D0 IV | 2 | H | H | t-BuO | Me | i-Pro | H | F | R | HCl |
| C28 | 33.6 mg/kg | D0 IV | 2 | H | H | t-BuO | Me | Me | H | CF$_3$ | R | MeSO$_3$H |
| C29 | 33.6 mg/kg | D0 IV | 2 | H | H | t-BuO | Me | Me | H | CHF$_2$ | R, S | HCl |
| C30 | 33.6 mg/kg | D0 IV | 3 | H | H | t-BuO | Me | Me | H | F | R, S | MeSO$_3$H |
| C31 | 33.6 mg/kg | D0 IV | 4 | H | H | t-BuO | Me | Me | H | F | S | sulfuric acid |

| Compd. No. | Tumor volume (mm$^3$) (D0) | Tumor volume (mm$^3$) (D20) | T/C (%) D20 | Tumor inhibitory percent (%)$^\Delta$ D20 | Weight change (%) D6 |
|---|---|---|---|---|---|
| the control group | 110.5 ± 4.4 | 870.5 ± 60.5 | — | — | −16 |
| docetaxel | 111.5 ± 1.3 | 81.4 ± 25.1 | −27 | 127 | −12.3 |
| C4 | 113.7 ± 2.9 | 26.6 ± 12.4 | −77 | 177 | −12.5 |

TABLE 5-continued

The inhibitory activity of the water soluble docetaxel derivatives and docetaxel
on subcutaneously xenografted tumor of human prostate cancer PC-3 in nude mice.

|  |  |  |  |  |  |
|---|---|---|---|---|---|
| C5 | 113.4 ± 3.1 | 26.8 ± 12.6 | −76 | 175 | −12.4 |
| C6 | 113.8 ± 3.0 | 27.0 ± 12.3 | −76 | 175 | −12.6 |
| C25 | 113.8 ± 3.0 | 30.4 ± 11.1 | −62 | 143 | −13.6 |
| C26 | 114.4 ± 2.8 | 32.4 ± 13.5 | −52 | 120 | −14.1 |
| C27 | 116.3 ± 3.7 | 35.3 ± 14.7 | −44 | 101 | −14.4 |
| C28 | 113.5 ± 2.8 | 34.5 ± 12.6 | −46 | 105 | −13.9 |
| C29 | 116.7 ± 3.1 | 36.8 ± 13.4 | −37 | 85 | −15.1 |
| C30 | 118.2 ± 4.8 | 41.5 ± 14.7 | −28 | 64 | −15.4 |
| C31 | 114.7 ± 3.5 | 52.4 ± 12.5 | −20 | 45 | −15.8 |

D0: the time of administration for the first time;
$\Delta P_{(D20)} = 0.000$, compared to the control, using Student's t-test.
The numbers of mice at the beginning of the experiment: n = 10 in the control group, and n = 6 in the administered group.
C* is the configuration of the chiral carbon in the side chain of an amino acid.
Conclusion: the water soluble docetaxel derivatives have an inhibitory effect on human prostate cancer PC-3.

6.3. Test of the Inhibitory Activity of the Water Soluble Cabazitaxel Derivatives on to Subcutaneously Xenografted Tumor of Human Prostate Cancer PC-3 in Nude Mice Purpose: to evaluate and compare the inhibitory activity of the water soluble cabazitaxel derivatives and cabazitaxel on subcutaneously xenografted tumor of human prostate cancer PC-3 in nude mice.

Dosage Regimen and Experimental Procedures:

Human prostate cancer PC-3 cells were subcutaneously inoculated into nude mice. After the tumor volume reached 100-150 mm³, the animals were randomly divided into several groups, and administered with the water soluble cabazitaxel derivatives of the following formula and cabazitaxel, respectively once on the same day (D0). The dosage and dosage regimen are shown in following table 6. The tumor volume was measured 2-3 times per week, the animals were weighed and the data were recorded until day 20 (D20) after grouping.

The tumor volume (V) was calculated according to the equation: $V = \frac{1}{2} \times a \times b^2$, wherein a and b represent the length and the width, respectively.

$T/C (\%) = (T - T_0)/(C - C_0) \times 100$, wherein T and C represent the tumor volume at the end of the experiment; and $T_0$ and $C_0$ represent the tumor volume at the beginning of the experiment.

The antitumor activity data are shown in following Table 6:

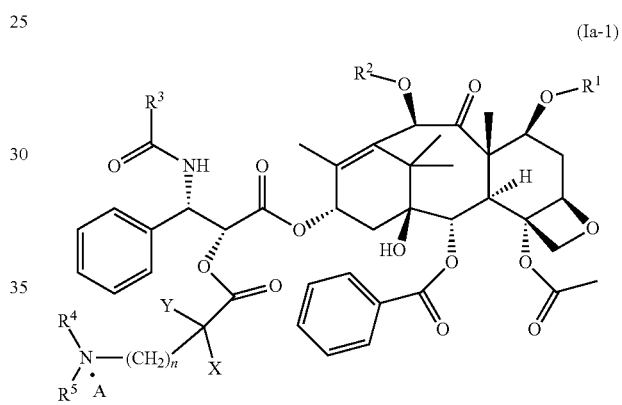

(Ia-1)

TABLE 6

The inhibitory activity of the water soluble cabazitaxel derivatives and cabazitaxel
on subcutaneously xenografted tumor of human prostate cancer PC-3 in nude mice.

| Compd. No. | Dosage | Time and route of administration | n | R¹ | R² | R³ | R⁴ | R⁵ | X | Y | C* | A |
|---|---|---|---|---|---|---|---|---|---|---|---|---|
| the control group | — | D0 IV | — | — | — | — | — | — | — | — | — | — |
| cabazitaxel | 7 mg/kg | D0 IV | — | — | — | — | — | — | — | — | — | — |
| C7 | 13 mg/kg | D0 IV | 2 | Me | Me | t-BuO | Me | Me | H | F | R | MeSO₃H |
| C8 | 13 mg/kg | D0 IV | 2 | Me | Me | t-BuO | Me | Me | H | F | S | MeSO₃H |
| C9 | 13 mg/kg | D0 IV | 2 | Me | Me | t-BuO | Me | Me | H | F | R, S | MeSO₃H |
| C32 | 13 mg/kg | D0 IV | 2 | Me | Me | t-BuO | Et | Me | H | F | R | maleic acid |
| C33 | 13 mg/kg | D0 IV | 2 | Me | Me | t-BuO | Et | Et | H | F | R | MeSO₃H |
| C34 | 13 mg/kg | D0 IV | 2 | Me | Me | t-BuO | Me | i-Pro | H | F | R | HCl |
| C35 | 13 mg/kg | D0 IV | 2 | Me | Me | t-BuO | Me | Me | H | CF₃ | R | MeSO₃H |
| C36 | 13 mg/kg | D0 IV | 2 | Me | Me | t-BuO | Me | Me | H | CHF₂ | R | p-toluene sulfonic acid |
| C37 | 13 mg/kg | D0 IV | 3 | Me | Me | t-BuO | Me | Me | H | F | R | HCl |
| C38 | 13 mg/kg | D0 IV | 4 | Me | Me | t-BuO | Me | Me | H | F | R | sulfuric acid |

TABLE 6-continued

The inhibitory activity of the water soluble cabazitaxel derivatives and cabazitaxel on subcutaneously xenografted tumor of human prostate cancer PC-3 in nude mice.

| Compd. No. | Tumor volume (mm³) (D0) | Tumor volume (mm³) (D20) | T/C (%) D20 | Tumor inhibitory percent (%)$^\Delta$ D20 | Weight change (%) D6 |
|---|---|---|---|---|---|
| the control group | 111.3 ± 3.8 | 868.4 ± 58.7 | — | — | −17 |
| cabazitaxel | 111.7 ± 1.8 | 79.9 ± 24.8 | −27 | 127 | −13.8 |
| C7 | 111.5 ± 2.2 | 31.5 ± 11.8 | −67 | 154 | −14.2 |
| C8 | 111.9 ± 2.0 | 32.1 ± 12.1 | −66 | 151 | −14.4 |
| C9 | 111.4 ± 2.3 | 32.5 ± 11.6 | −66 | 151 | −14.4 |
| C32 | 112.4 ± 3.0 | 35.8 ± 12.7 | −56 | 128 | −14.7 |
| C33 | 112.0 ± 2.4 | 38.6 ± 13.4 | −50 | 114 | −15.1 |
| C34 | 111.7 ± 3.2 | 42.8 ± 11.9 | −45 | 101 | −15.4 |
| C35 | 110.2 ± 4.6 | 42.3 ± 12.6 | −46 | 105 | −15.8 |
| C36 | 116.7 ± 3.9 | 48.4 ± 14.7 | −37 | 85 | −16.1 |
| C37 | 112.9 ± 4.4 | 55.3 ± 13.8 | −28 | 64 | −16.6 |
| C38 | 111.9 ± 3.7 | 66.8 ± 12.4 | −20 | 46 | −16.8 |

D0: the time of administration for the first time;
$^\Delta P_{(D20)} = 0.000$, compared to the control, using Student's t-test.
The numbers of mice at the beginning of the experiment: n = 10 in the control group, and n = 6 in the administered group.
C* is the configuration of the chiral carbon in the side chain of an amino acid.
Conclusion: the water soluble cabazitaxel derivatives have an inhibitory effect on human prostate cancer PC-3.

D0: the time of administration for the first time:
Δ: $P_{(D20)}$=0.000, compared to the control using Student's t-test.

The numbers of mice at the beginning of the experiment: n=10 in the control group, and n=6 in the administered group.

C* is the configuration of the chiral carbon in the side chain of an amino acid.

Conclusion: the water soluble cabazitaxel derivatives have an inhibitory effect on human prostate cancer PC-3.

6.4. Test of the Inhibitory Activity of the Water Soluble Larotaxel and Tesetaxel Derivatives on Subcutaneously Xenografted Tumor of Human Non-Small Cell Lung Cancer NCI-H446 in Nude Mice Purpose: to evaluate and compare the inhibitory activity of the water soluble larotaxel and tesetaxel derivatives on subcutaneously xenografted tumor of human non-small cell lung cancer NCI-H446 in nude mice.

Dosage Regimen and Experimental Procedures:

Human non-small cell lung cancer NCI-H446 cells were subcutaneously inoculated into nude mice. After the tumor volume reached 100-150 mm³, the animals were randomly divided into several groups, and administered with the water soluble larotaxel and tesetaxel derivatives of the following formulae, larotaxel, and tesetaxel, respectively once on the same day (D0). The dosage and dosage regimen are shown in the following table. The tumor volume was measured 2-3 times per week, the animals were weighed and the data were recorded until day 20 (D20) after grouping.

The tumor volume (V) was calculated according to the equation: V=½×a×b², wherein a and b represent the length and the width, respectively.

T/C (%)=(T−T₀)/(C−C₀)×100, wherein T and C represent the tumor volume at the end of the experiment; and T₀ and C₀ represent the tumor volume at the beginning of the experiment.

The antitumor activity data are shown in following Table 7:

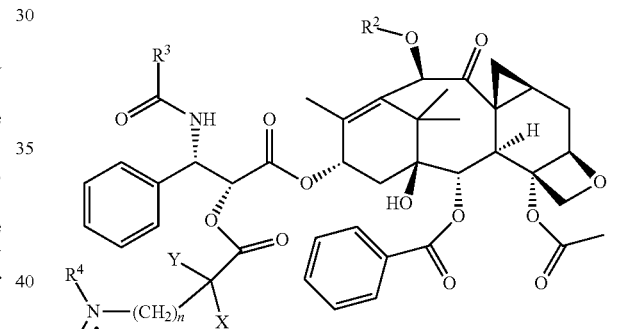

(Ia-2)

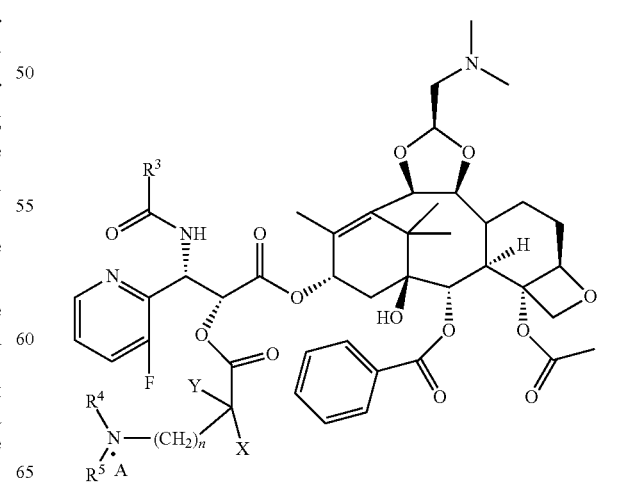

(Ia-3)

TABLE 7

The inhibitory activity of the water soluble larotaxel and tesetaxel derivatives, larotaxel, and tesetaxel on subcutaneously xenografted tumor of human non-small cell lung cancer NCI-H446 in nude mice.

| Compd. No. | Dosage | Time and route of administration | Type of the parent ring | n | $R^2$ | $R^3$ | $R^4$ | $R^5$ | X | Y | C* | A |
|---|---|---|---|---|---|---|---|---|---|---|---|---|
| The control group | — | D0 IV | — | — | — | — | — | — | — | — | — | — |
| larotaxel | 7 mg/kg | D0 IV | I-2 | — | Ac | t-BuO | — | — | — | — | — | — |
| tesetaxel | 8 mg/kg | D0 IV | I-3 | — | — | t-BuO | — | — | — | — | — | — |
| C39 | 12 mg/kg | D0 IV | I-2 | 2 | Ac | t-BuO | Me | Me | H | F | R | HCl |
| C40 | 12 mg/kg | D0 IV | I-2 | 2 | Ac | t-BuO | Et | Me | H | F | R, S | HCl |
| C41 | 12 mg/kg | D0 IV | I-2 | 2 | Ac | t-BuO | Me | i-Pro | H | $CF_3$ | R, S | maleic acid |
| C42 | 12 mg/kg | D0 IV | I-2 | 3 | Ac | t-BuO | Me | Me | H | F | S | phosphoric acid |
| C43 | 12 mg/kg | D0 IV | I-3 | 2 | — | t-BuO | Me | Me | H | F | R | HCl |
| C44 | 12 mg/kg | D0 IV | I-3 | 2 | — | t-BuO | Et | Et | H | F | S | HCl |
| C45 | 12 mg/kg | D0 IV | I-3 | 2 | — | t-BuO | Me | i-Pro | H | $CF_3$ | R, S | succinic acid |
| C46 | 12 mg/kg | D0 IV | I-3 | 3 | — | t-BuO | —$CH_2CH_2CH_2CH_2$— | | H | F | R, S | sulfuric acid |

| | Anti-tumor activity data | | | | |
|---|---|---|---|---|---|
| Compd. No. | Tumor volume ($mm^3$) (D0) | Tumor volume ($mm^3$) (D20) | T/C (%) D20 | Tumor inhibitory percent (%)$^\Delta$ D20 | Weight change (%) D5 |
| The control group | 111.3 ± 3.8 | 868.4 ± 58.7 | — | — | −15.5 |
| larotaxel | 110.9 ± 2.4 | 33.3 ± 12.4 | −64 | 153 | −8.4 |
| tesetaxel | 112.8 ± 2.2 | 33.7 ± 12.1 | −58 | 146 | −7.4 |
| C39 | 111.5 ± 2.2 | 34.9 ± 13.3 | −62 | 148 | −8.5 |
| C40 | 112.4 ± 1.8 | 43.2 ± 12.7 | −51 | 122 | −9.1 |
| C41 | 109.8 ± 2.9 | 51.7 ± 11.9 | −34 | 67 | −10.5 |
| C42 | 109.8 ± 2.9 | 51.7 ± 9.8 | −22 | 53 | −13.8 |
| C43 | 111.5 ± 2.2 | 31.8 ± 11.1 | −61 | 153 | −8.2 |
| C44 | 113.6 ± 2.8 | 41.3 ± 10.9 | −49 | 123 | −9.4 |
| C45 | 112.3 ± 3.1 | 53.4 ± 12.4 | −34 | 85 | −11.4 |
| C46 | 111.7 ± 2.8 | 61.2 ± 14.2 | −23 | 58 | −14.4 |

D0: the time of administration for the first time;
$^\Delta P_{(D20)} = 0.000$, compared to the control, using Student's t-test.
The numbers of mice at the beginning of the experiment: n = 10 in the control group, and n = 6 in the administered group.
C* is the configuration of the chiral carbon in the side chain of an amino acid.
Conclusion: the water soluble larotaxel and tesetaxel derivatives have an inhibitory effect on human non-small cell lung cancer NCI-H446.

According to the results in the further experimentation, the inventors found that the taxane derivatives of the present invention have good water solubility, and can be dissociated in blood plasma to release a taxane parent drug, and thus are suitable as antitumor prodrugs.

What is claimed is:

1. A water soluble taxane derivative of general formula (I-1), (I-2) or (I-3):

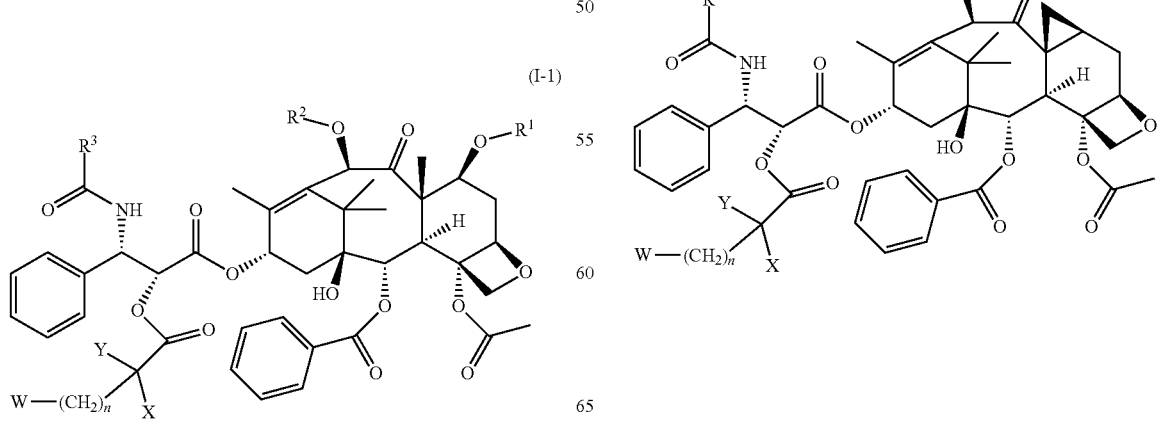

-continued (I-3)

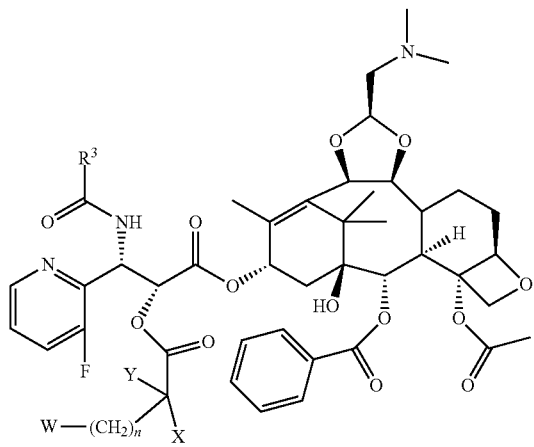

wherein,
R¹ is H or methyl;
R² is H, methyl or acetyl;
R³ is phenyl or OC(CH₃)₃;
X is H, C₁₋₆ alkyl or F;
Y is F or C₁₋₆ alkyl substituted with one or more F;
n is 1, 2, 3, 4, 5 or 6;
W is NR⁴R⁵.A or

R⁴ and R⁵ are each independently H, C₁₋₆ alkyl optionally substituted with phenyl, or C₃₋₆ cycloalkyl;
m is 0, 1, 2 or 3; and
A is a pharmaceutically acceptable acid.

2. The water soluble taxane derivative according to claim 1, characterized in that in general formula (I-1),
R¹ is H, R² is acetyl, and R³ is phenyl;
R¹ is H, R² is H, and R³ is OC(CH₃)₃; or
R¹ is methyl, R² is methyl, and R³ is OC(CH₃)₃.

3. The water soluble taxane derivative according to claim 1, characterized in that in general formula (I-2),
R² is acetyl and R³ is OC(CH₃)₃.

4. The water soluble taxane derivative according to claim 1, characterized in that in general formula (I-3),
R³ is OC(CH₃)₃.

5. The water soluble taxane derivative according to claim 1, characterized in that the C₁₋₆ alkyl is methyl, ethyl, propyl, isopropyl, butyl or isobutyl.

6. The water soluble taxane derivative according to claim 1, characterized in that the C₃₋₆ cycloalkyl is cyclopropyl, cyclobutyl, cyclopentyl or cyclohexyl.

7. The water soluble taxane derivative according to claim 1, characterized in that X is H, methyl or F.

8. The water soluble taxane derivative according to claim 1, characterized in that Y is F, CF₃ or CHF₂.

9. The water soluble taxane derivative according to claim 1, characterized in that R⁴ and R⁵ are each independently H, methyl, ethyl, propyl, isopropyl, butyl, isobutyl, benzyl, cyclopropyl, cyclobutyl, cyclopentyl or cyclohexyl.

10. The water soluble taxane derivative according to claim 1, characterized in that:

X is H, methyl or F;
Y is F, CF₃ or CHF₂;
R⁴ and R⁵ are each independently H, methyl, ethyl, propyl, isopropyl, butyl, isobutyl, benzyl, cyclopropyl, cyclobutyl, cyclopentyl or cyclohexyl.

11. The water soluble taxane derivative according to claim 1, characterized in that the pharmaceutically acceptable acid is hydrochloric acid, hydrobromic acid, sulfuric acid, phosphoric acid, carbonic acid, acetic acid, propionic acid, methanesulfonic acid, lactic acid, benzensulfonic acid, p-toluene sulfonic acid, succinic acid, maleic acid, fumaric acid, tartaric acid, citric acid or malic acid.

12. The water soluble taxane derivative according to claim 1, characterized in that when X and Y are different, the carbon atom to which both X and Y are attached is in a single R configuration, in a single S configuration, or in both R and S configurations.

13. The water soluble taxane derivative according to claim 1, which is selected from the group consisting of:
2'-O-[4-N,N-dimethylamino-2(R)-fluorobutyryl]paclitaxel hydrochloride;
2'-O-[4-N,N-dimethylamino-2(R)-fluorobutyryl]paclitaxel methanesulfonate;
2'-O-[4-N,N-dimethylamino-2(R,S)-fluorobutyryl]paclitaxel hydrochloride;
2'-O-[4-N,N-dimethylamino-2(R,S)-difluoromethylbutyryl]paclitaxel citrate;
2'-O-[4-N,N-dimethylamino-2(R)-fluorobutyryl]docetaxel hydrochloride;
2'-O-[4-N,N-dimethylamino-2(R)-fluorobutyryl]docetaxel methanesulfonate;
2'-O-[4-amino-2(R,S)-trifluoromethylbutyryl]docetaxel methanesulfonate;
2'-O-[4-N,N-dimethylamino-2(R,S)-fluorobutyryl]cabazitaxel hydrochloride;
2'-O-[4-N,N-dimethylamino-2(R)-fluorobutyryl]larotaxel hydrochloride;
2'-O-[4-N,N-dimethylamino-2(R)-fluorobutyryl]tesetaxel hydrochloride;
2'-O-[4-N,N-dimethylamino-2(S)-fluorobutyryl]paclitaxel hydrochloride;
2'-O-[4-N,N-dimethylamino-2(S)-fluorobutyryl]docetaxel hydrochloride;
2'-O-[4-N,N-dimethylamino-2(R,S)-fluorobutyryl]docetaxel hydrochloride;
2'-O-[4-N,N-dimethylamino-2(R)-fluorobutyryl]cabazitaxel hydrochloride;
2'-O-[4-N,N-dimethylamino-2(S)-fluorobutyryl]cabazitaxel hydrochloride;
2'-O-[4-amino-2(R)-difluoromethylbutyryl]cabazitaxel sodium bisulfate salt;
2'-O-[4-N,N-diethylamino-2-methyl-2(R)-2-trifluoromethylbutyryl]cabazitaxel methanesulfonate;
2'-O-[4-N-methyl-N-ethylamino-2(R)-2-difluoroethylvaleryl]docetaxel hydrochloride;
2'-O-[4-N,N-dimethylamino-2(R)-fluorovaleryl]docetaxel methanesulfonate;
2'-O-[4-(aziridin-1-yl)amino-2,2-difluoroheptanoyl]docetaxel methanesulfonate;
2'-O-[4-N-methyl-N-cyclopentylamino-2-trifluoromethyl-2-fluorooctanoyl]paclitaxel methanesulfonate;
2'-O-[4-N,N-dimethylamino-2(R)-fluorovaleryl]larotaxel methanesulfonate;
2'-O-[4-N,N-dimethylamino-2(R)-fluorovaleryl]tesetaxel methanesulfonate;
2'-O-[4-N,N-dimethylamino-2(S)-fluorobutyryl]paclitaxel methanesulfonate;

2'-O-[4-N,N-dimethylamino-2(R,S)-fluorobutyryl]paclitaxel methanesulfonate;
2'-O-[4-N,N-dimethylamino-2(S)-fluorobutyryl]docetaxel methanesulfonate;
2'-O-[4-N,N-dimethylamino-2(R,S)-fluorobutyryl]docetaxel methanesulfonate;
2'-O-[4-N,N-dimethylamino-2(R)-fluorobutyryl]cabazitaxel methanesulfonate;
2'-O-[4-N,N-dimethylamino-2(S)-fluorobutyryl]cabazitaxel methanesulfonate;
2'-O-[4-N,N-dimethylamino-2(R,S)-fluorobutyryl]cabazitaxel methanesulfonate;
2'-O-[4-amino-2(R)-difluoromethylbutyryl]cabazitaxel sulfate;
2'-O-[4-N,N-diethylamino-2-methyl-2(R)-2-trifluoromethylbutyryl]cabazitaxel hydrochloride;
2'-O-[4-N-methyl-N-ethylamino-2(R)-2-difluoroethylvaleryl]docetaxel methanesulfonate;
2'-O-[4-N,N-dimethylamino-2(R)-fluorovaleryl]docetaxel hydrochloride;
2'-O-[4-(aziridin-1-yl)amino-2,2-difluoroheptanoyl]docetaxel hydrochloride;
2'-O-[4-N-methyl-N-cyclopentylamino-2-trifluoromethyl-2-fluorooctanoyl]paclitaxel hydrochloride;
2'-O-[4-N,N-dimethylamino-2(R)-fluorovaleryl]larotaxel hydrochloride;
2'-O-[4-N,N-dimethylamino-2(R)-fluorovaleryl]tesetaxel hydrochloride;
2'-O-[4-N-methyl-N-ethylamino-2(R)-fluorobutyryl]paclitaxel methanesulfonate;
2'-O-[4-N,N-diethylamino-2(S)-fluorobutyryl]paclitaxel fumarate;
2'-O-[4-N-methyl-N-isopropylamino-2(R,S)-fluorobutyryl]paclitaxel hydrochloride;
2'-O-[4-N,N-dimethylamino-2(R,S)-2-trifluoromethylbutyryl]paclitaxel p-toluene sulfonate;
2'-O-[4-N,N-dimethylamino-2(R,S)-2-difluoromethylbutyryl]paclitaxel hydrochloride;
2'-O-[4-N,N-dimethylamino-2(R)-fluorovaleryl]paclitaxel maleate;
2'-O-[4-N,N-dimethylamino-2(S)-2-difluoromethylhexanoyl]paclitaxel sulfate;
2'-O-[4-N-methyl-N-ethylamino-2(R)-fluorobutyryl]docetaxel methanesulfonate;
2'-O-[4-N,N-diethylamino-2(S)-fluorobutyryl]docetaxel maleate;
2'-O-[4-N-methyl-N-isopropylamino-2(R)-fluorobutyryl]docetaxel hydrochloride;
2'-O-[4-N,N-dimethylamino-2(R)-2-trifluoromethylbutyryl]docetaxel methanesulfonate;
2'-O-[4-N,N-dimethylamino-2(R,S)-2-difluoromethylbutyryl]docetaxel hydrochloride;
2'-O-[4-N,N-dimethylamino-2(R,S)-fluorovaleryl]docetaxel methanesulfonate;
2'-O-[4-N,N-dimethylamino-2(S)-fluorohexanoyl]docetaxel sulfate;
2'-O-[4-N-methyl-N-ethylamino-2(R)-fluorobutyryl]cabazitaxel maleate;
2'-O-[4-N,N-diethylamino-2(R)-fluorobutyryl]cabazitaxel methanesulfonate;
2'-O-[4-N-methyl-N-isopropylamino-2(R)-fluorobutyryl]cabazitaxel hydrochloride;
2'-O-[4-N,N-dimethylamino-2(R)-2-trifluoromethylbutyryl]cabazitaxel methanesulfonate;
2'-O-[4-N,N-dimethylamino-2(R)-2-difluoromethylbutyryl]cabazitaxel p-toluene sulfonate;
2'-O-[4-N,N-dimethylamino-2(R)-fluorovaleryl]cabazitaxel hydrochloride;
2'-O-[4-N,N-dimethylamino-2(R)-fluorohexanoyl]cabazitaxel sulfate;
2'-O-[4-N-methyl-N-ethylamino-2(R,S)-fluorobutyryl]larotaxel hydrochloride;
2'-O-[4-N-methyl-N-isopropylamino-2(R,S)-2-trifluoromethylbutyryl]larotaxel maleate;
2'-O-[4-N,N-dimethylamino-2(S)-fluorovaleryl]larotaxel phosphate;
2'-O-[4-N,N-diethylamino-2(S)-fluorobutyryl]tesetaxel hydrochloride;
2'-O-[4-N-methyl-N-isopropylamino-2(R,S)-2-trifluoromethylbutyryl]tesetaxel succinate;
2'-O-[4-(pyrrolidin-1-yl)amino-2(R,S)-fluorovaleryl]tesetaxel sulfate;
2'-O-[4-N,N-diethylamino-2(R)-fluorobutyryl]paclitaxel hydrochloride;
2'-O-[3-N,N-dimethylamino-2(R,S)-fluoropropionyl]paclitaxel hydrochloride;
2'-O-[4-N-benzylamino-2(S)-fluorobutyryl]docetaxel hydrochloride;
2'-O-[3-(N,N-diethyl)amino-2(R,S)-trifluoromethylpropionyl]docetaxel hydrochloride;
2'-O-[4-(N-methyl)amino-2(R)-trifluoromethylbutyryl]paclitaxel hydrochloride;
2'-O-[3-(N-isopropyl)amino-2(R,S)-difluoromethylpropionyl]cabazitaxel hydrochloride;
2'-O-[5-(N,N-dimethyl)amino-2(R)-fluorovaleryl]paclitaxel hydrochloride;
2'-O-[4-(N,N-dimethyl)amino-2(S)-trifluoromethylbutyryl]cabazitaxel hydrochloride;
2'-O-[4-(N-isopropyl)amino-2(R,S)-trifluoromethylbutyryl]paclitaxel hydrochloride;
2'-O-[5-N,N-dimethylamino-2(S)-trifluoromethylvaleryl]docetaxel hydrochloride;
2'-O-[4-N-benzylamino-2-methyl-2(R,S)-fluorobutyryl]paclitaxel hydrochloride;
2'-O-[4-N,N-dimethylamino-2(R)-difluoromethylbutyryl]docetaxel hydrochloride;
2'-O-[3-cyclopentylamino-2-ethyl-2(R,S)-trifluoromethylpropionyl]docetaxel hydrochloride;
2'-O-[5-N-benzylamino-2-benzyl-2(R)-difluoromethylvaleryl]cabazitaxel hydrochloride;
2'-O-[4-(4-piperidin-1-yl)-2(S)-trifluoromethylbutyryl]cabazitaxel hydrochloride; and
2'-O-[4-N,N-dimethylamino-2(S)-fluorobutyryl]larotaxel hydrochloride; and
2'-O-[4-N,N-dimethylamino-2(R)-fluorobutyryl]tesetaxel hydrochloride.

14. A method for treating tumor, comprising administering to a patient the water soluble taxane derivative according to claim 1.

* * * * *